(12) United States Patent
Keller et al.

(10) Patent No.: US 11,857,432 B2
(45) Date of Patent: Jan. 2, 2024

(54) EXPANDABLE IMPLANT ASSEMBLY

(71) Applicant: LIFE SPINE, INC., Huntley, IL (US)

(72) Inventors: Katrina Robin Keller, Saint Charles, IL (US); Madeline Wolters, Carol Stream, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 16/847,187

(22) Filed: Apr. 13, 2020

(65) Prior Publication Data

US 2021/0315707 A1 Oct. 14, 2021

(51) Int. Cl.
*A61F 2/44* (2006.01)
*A61F 2/30* (2006.01)

(52) U.S. Cl.
CPC .. *A61F 2/4425* (2013.01); *A61F 2002/30578* (2013.01); *A61F 2002/443* (2013.01)

(58) Field of Classification Search
CPC .............. A61F 2/4425; A61F 2002/443; A61F 2/4455–2/447; A61B 17/80–17/8095
See application file for complete search history.

(56) References Cited

U.S. PATENT DOCUMENTS

| | | | |
|---|---|---|---|
| 904,434 A | 11/1908 | Huff | |
| 1,925,385 A | 9/1933 | Humes | |
| 3,846,846 A | 11/1974 | Fischer | |
| 4,466,426 A | 8/1984 | Blackman | |
| 4,636,217 A | 1/1987 | Ogilvie et al. | |
| 4,743,256 A | 5/1988 | Brantigan | |
| 4,863,476 A | 9/1989 | Shepperd | |
| 5,098,435 A | 3/1992 | Stednitz et al. | |

(Continued)

FOREIGN PATENT DOCUMENTS

| | | |
|---|---|---|
| CN | 102427769 A | 4/2012 |
| CN | 205866898 U | 1/2017 |

(Continued)

OTHER PUBLICATIONS

Bacfuse® Spinous Process Fusion Plate Surgical Technique, 2011, Pioneer Surgical, 12 pages.

(Continued)

*Primary Examiner* — Eduardo C Robert
*Assistant Examiner* — Michelle C Eckman
(74) *Attorney, Agent, or Firm* — Foley & Lardner LLP

(57) ABSTRACT

An expandable implant includes an upper plate configured to receive a first anchoring member, an upper support mechanically coupled to the upper plate, a lower plate configured to receive a second anchoring member, and a lower support mechanically coupled to the lower plate. The implant further includes a control member including a shaft and configured to control movement between the upper support and the lower support, a front portion configured engage the upper support and the lower support and further configured to receive the head of the control member, and a rear portion configured engage the upper support and the lower support and further configured to engage a portion of the shaft, wherein turning the control member causes the front portion to move in a direction towards the rear portion, such that the upper support moves relative to the lower support in a direction away from the lower support.

14 Claims, 27 Drawing Sheets

(56) References Cited

U.S. PATENT DOCUMENTS

| | | |
|---|---|---|
| 5,192,327 A | 3/1993 | Brantigan |
| 5,236,460 A | 8/1993 | Barber |
| 5,390,683 A | 2/1995 | Pisharodi |
| 5,522,899 A | 6/1996 | Michelson |
| 5,609,635 A | 3/1997 | Michelson |
| 5,645,599 A | 7/1997 | Samani |
| 5,658,335 A | 8/1997 | Allen |
| 5,658,337 A | 8/1997 | Kohrs et al. |
| 5,776,199 A | 7/1998 | Michelson |
| 5,836,948 A | 11/1998 | Zucherman et al. |
| 5,860,977 A | 1/1999 | Zucherman et al. |
| 5,876,404 A | 3/1999 | Zucherman et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,193 A | 6/2000 | Hochshuler et al. |
| 6,113,638 A | 9/2000 | Williams et al. |
| 6,126,689 A | 10/2000 | Brett |
| 6,129,763 A | 10/2000 | Chauvin et al. |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,290,724 B1 | 9/2001 | Marino |
| 6,302,914 B1 | 10/2001 | Michelson |
| 6,375,682 B1 | 4/2002 | Fleischmann et al. |
| 6,409,766 B1 | 6/2002 | Brett |
| 6,443,989 B1 | 9/2002 | Jackson |
| 6,443,990 B1 | 9/2002 | Aebi et al. |
| 6,447,544 B1 | 9/2002 | Michelson |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,576,016 B1 | 6/2003 | Hochshuler et al. |
| 6,613,091 B1 | 9/2003 | Zdeblick et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,752,832 B2 | 6/2004 | Neumann |
| 6,773,460 B2 | 8/2004 | Jackson |
| 6,796,983 B1 | 9/2004 | Zucherman et al. |
| 6,800,092 B1 | 10/2004 | Williams et al. |
| 6,849,093 B2 | 2/2005 | Michelson |
| 7,001,385 B2 | 2/2006 | Bonutti |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,214,243 B2 | 5/2007 | Taylor |
| 7,217,291 B2 | 5/2007 | Zucherman et al. |
| 7,220,280 B2 | 5/2007 | Kast et al. |
| 7,250,055 B1 | 7/2007 | Vanderwalle |
| 7,473,276 B2 | 1/2009 | Aebi et al. |
| 7,503,933 B2 | 3/2009 | Michelson |
| 7,621,950 B1 | 11/2009 | Globerman et al. |
| 7,695,513 B2 | 4/2010 | Zucherman et al. |
| 7,722,674 B1 | 5/2010 | Grotz |
| 7,727,280 B2 | 6/2010 | McLuen |
| 7,731,751 B2 | 6/2010 | Butler et al. |
| 7,789,914 B2 | 9/2010 | Michelson |
| D626,233 S | 10/2010 | Cipoletti et al. |
| 7,824,427 B2 | 11/2010 | Perez-Cruet et al. |
| 7,828,849 B2 | 11/2010 | Lim |
| 7,837,734 B2 | 11/2010 | Zucherman et al. |
| 7,846,188 B2 | 12/2010 | Moskowitz et al. |
| 7,850,733 B2 | 12/2010 | Baynham et al. |
| 7,854,766 B2 | 12/2010 | Moskowitz et al. |
| 7,867,277 B1 | 1/2011 | Tohmeh |
| 7,879,098 B1 | 2/2011 | Simmons, Jr. |
| 7,942,903 B2 | 5/2011 | Moskowitz et al. |
| 7,959,675 B2 | 6/2011 | Gately |
| 7,972,363 B2 | 7/2011 | Moskowitz et al. |
| 8,016,861 B2 | 9/2011 | Mitchell et al. |
| 8,021,430 B2 | 9/2011 | Michelson |
| 8,048,117 B2 | 11/2011 | Zucherman et al. |
| 8,062,375 B2 | 11/2011 | Glerum et al. |
| 8,070,817 B2 | 12/2011 | Gradl et al. |
| 8,071,007 B1 | 12/2011 | Teoh et al. |
| 8,105,382 B2 | 1/2012 | Olmos et al. |
| 8,187,332 B2 | 5/2012 | McLuen |
| 8,231,656 B2 | 7/2012 | Lee et al. |
| 8,241,330 B2 | 8/2012 | Lamborne et al. |
| 8,241,364 B2 | 8/2012 | Hansell et al. |
| 8,252,060 B2 | 8/2012 | Hansell et al. |
| 8,257,370 B2 | 9/2012 | Moskowitz et al. |
| 8,267,939 B2 | 9/2012 | Cipoletti et al. |
| 8,303,663 B2 | 11/2012 | Jimenez et al. |
| 8,308,804 B2 | 11/2012 | Krueger |
| 8,343,190 B1 | 1/2013 | Mueller et al. |
| 8,353,913 B2 | 1/2013 | Moskowitz et al. |
| 8,353,963 B2 | 1/2013 | Glerum |
| 8,366,777 B2 | 2/2013 | Matthis et al. |
| 8,382,801 B2 | 2/2013 | Lamborne et al. |
| 8,382,842 B2 | 2/2013 | Greenhalgh et al. |
| 8,388,686 B2 | 3/2013 | Aebi et al. |
| 8,394,129 B2 | 3/2013 | Lopez et al. |
| 8,398,713 B2 | 3/2013 | Weiman |
| 8,425,607 B2 | 4/2013 | Waugh et al. |
| 8,435,298 B2 | 5/2013 | Weiman |
| 8,444,696 B2 | 5/2013 | Michelson |
| 8,454,706 B2 | 6/2013 | De Beaubien |
| 8,491,659 B2 | 7/2013 | Weiman |
| 8,506,629 B2 | 8/2013 | Weiland |
| 8,518,120 B2 | 8/2013 | Glerum et al. |
| 8,529,628 B2 | 9/2013 | Marino et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,597,360 B2 | 12/2013 | McLuen et al. |
| 8,628,578 B2 | 1/2014 | Miller et al. |
| 8,632,595 B2 | 1/2014 | Weiman |
| 8,641,764 B2 | 2/2014 | Gately |
| 8,641,766 B2 | 2/2014 | Donner et al. |
| 8,663,332 B1 | 3/2014 | To et al. |
| 8,679,183 B2 | 3/2014 | Glerum et al. |
| 8,685,098 B2 | 4/2014 | Glerum et al. |
| 8,690,883 B2 | 4/2014 | Collins et al. |
| 8,702,798 B2 | 4/2014 | Matthis et al. |
| 8,709,086 B2 | 4/2014 | Glerum |
| 8,734,516 B2 | 5/2014 | Moskowitz et al. |
| 8,795,366 B2 | 8/2014 | Varela |
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,906,095 B2 | 12/2014 | Christensen et al. |
| 8,926,704 B2 | 1/2015 | Glerum et al. |
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 * | 5/2015 | Wolters ............ A61B 17/8858 623/17.15 |
| 9,034,045 B2 | 5/2015 | Davenport et al. |
| 9,039,771 B2 | 5/2015 | Glerum et al. |
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |

(56) References Cited

U.S. PATENT DOCUMENTS

| | | |
|---|---|---|
| 9,149,367 B2 | 10/2015 | Davenport et al. |
| 9,186,258 B2 | 11/2015 | Davenport et al. |
| 9,186,262 B2 | 11/2015 | McLuen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,333,092 B2 | 5/2016 | To et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,474,622 B2 | 10/2016 | McLaughlin et al. |
| 9,480,579 B2 | 11/2016 | Davenport et al. |
| 9,486,325 B2 | 11/2016 | Davenport et al. |
| 9,486,326 B2 | 11/2016 | Gahman et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | McAtamney et al. |
| 9,532,821 B2 | 1/2017 | Moskowitz et al. |
| 9,532,883 B2 | 1/2017 | McLuen et al. |
| 9,539,103 B2 | 1/2017 | McLaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 * | 5/2018 | Daffinson ............... A61F 2/447 |
| 9,968,462 B2 | 5/2018 | Weiman |
| 9,974,665 B2 | 5/2018 | McLuen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | McLuen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | McLaughlin et al. |
| 10,052,213 B2 | 8/2018 | Glerum et al. |
| 10,058,433 B2 | 8/2018 | Lechmann et al. |
| 10,064,742 B2 | 9/2018 | Taylor et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | McLuen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 | 11/2018 | Dewey et al. |
| 10,143,500 B2 | 12/2018 | Niemiec et al. |
| 10,143,569 B2 | 12/2018 | Weiman et al. |
| 10,154,911 B2 | 12/2018 | Predick et al. |
| 10,159,583 B2 | 12/2018 | Dietzel et al. |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | McLuen et al. |
| 10,299,934 B2 | 5/2019 | Seifert et al. |
| 10,307,268 B2 | 6/2019 | Moskowitz et al. |
| 10,350,085 B2 | 7/2019 | Glerum et al. |
| 10,376,386 B2 | 8/2019 | Moskowitz et al. |
| 10,383,741 B2 | 8/2019 | Butler et al. |
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,449,058 B2 | 10/2019 | Lechmann et al. |
| 10,470,894 B2 | 11/2019 | Foley et al. |
| 10,478,319 B2 | 11/2019 | Moskowitz et al. |
| 10,512,550 B2 | 12/2019 | Bechtel et al. |
| 10,531,895 B2 | 1/2020 | Weiman et al. |
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | McLuen et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,573 B2 | 7/2020 | Weiman et al. |
| 10,709,574 B2 | 7/2020 | McLuen et al. |
| 10,722,379 B2 | 7/2020 | McLaughlin et al. |
| 10,729,560 B2 | 8/2020 | Baker et al. |
| 10,729,562 B2 | 8/2020 | Knapp et al. |
| 10,736,754 B2 | 8/2020 | McLuen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |

(56) References Cited

U.S. PATENT DOCUMENTS

| | | |
|---|---|---|
| 10,786,364 B2 | 9/2020 | Davenport et al. |
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 | 6/2021 | Miller et al. |
| 11,051,951 B2 | 7/2021 | Robinson et al. |
| 11,065,128 B2 | 7/2021 | Zappacosta et al. |
| 2002/0010472 A1 | 1/2002 | Kuslich et al. |
| 2002/0029084 A1 | 3/2002 | Paul et al. |
| 2002/0128716 A1 | 9/2002 | Cohen et al. |
| 2002/0143343 A1 | 10/2002 | Castro |
| 2002/0143399 A1 | 10/2002 | Sutcliffe |
| 2002/0147461 A1 | 10/2002 | Aldrich et al. |
| 2002/0177897 A1 | 11/2002 | Michelson |
| 2003/0004576 A1 | 1/2003 | Thalgott |
| 2003/0040746 A1 | 2/2003 | Mitchell et al. |
| 2003/0040802 A1 | 2/2003 | Errico et al. |
| 2003/0176926 A1 | 9/2003 | Boehm et al. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0230309 A1 | 11/2004 | Dimauro et al. |
| 2004/0254643 A1 | 12/2004 | Jackson |
| 2005/0027362 A1 | 2/2005 | Williams et al. |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | McLuen |
| 2006/0122701 A1 | 6/2006 | Kiester |
| 2006/0189999 A1 | 8/2006 | Zwirkoski |
| 2006/0241601 A1 | 10/2006 | Trautwein et al. |
| 2006/0241621 A1 | 10/2006 | Moskowitz et al. |
| 2006/0253201 A1 | 11/2006 | McLuen |
| 2006/0264938 A1 | 11/2006 | Zucherman et al. |
| 2006/0265077 A1 | 11/2006 | Zwirkoski |
| 2007/0072475 A1 | 3/2007 | Justin et al. |
| 2007/0142915 A1 | 6/2007 | Altarac et al. |
| 2007/0213739 A1 | 9/2007 | Michelson |
| 2007/0244485 A1 | 10/2007 | Greenhalgh et al. |
| 2007/0270968 A1 | 11/2007 | Baynham et al. |
| 2008/0114367 A1 | 5/2008 | Meyer |
| 2008/0114453 A1 | 5/2008 | Francis |
| 2008/0114456 A1 | 5/2008 | Dewey et al. |
| 2008/0119853 A1 | 5/2008 | Felt et al. |
| 2008/0119945 A1 | 5/2008 | Frigg |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0243251 A1 | 10/2008 | Stad et al. |
| 2008/0288077 A1 | 11/2008 | Reo et al. |
| 2008/0312741 A1 | 12/2008 | Lee et al. |
| 2009/0005872 A1 | 1/2009 | Moumene et al. |
| 2009/0062833 A1 | 3/2009 | Song |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198338 A1 | 8/2009 | Phan |
| 2009/0198339 A1 | 8/2009 | Kleiner et al. |
| 2009/0222099 A1 | 9/2009 | Liu et al. |
| 2009/0312837 A1 | 12/2009 | Eisermann et al. |
| 2010/0082109 A1 | 4/2010 | Greenhalgh et al. |
| 2010/0103344 A1 | 4/2010 | Wang et al. |
| 2010/0179655 A1 | 7/2010 | Hansell et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234889 A1 | 9/2010 | Hess |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0046682 A1 | 2/2011 | Stephan et al. |
| 2011/0054538 A1 | 3/2011 | Zehavi et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144753 A1 | 6/2011 | Marchek et al. |
| 2011/0144755 A1 | 6/2011 | Baynham et al. |
| 2011/0166654 A1 | 7/2011 | Gately |
| 2011/0172709 A1 | 7/2011 | Lyons et al. |
| 2011/0172716 A1 | 7/2011 | Glerum |
| 2011/0172774 A1 | 7/2011 | Varela |
| 2011/0178599 A1 | 7/2011 | Brett |
| 2011/0184468 A1 | 7/2011 | Metcalf et al. |
| 2011/0190817 A1 | 8/2011 | Thommen et al. |
| 2011/0196494 A1 | 8/2011 | Yedlicka et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0035730 A1 | 2/2012 | Spann |
| 2012/0046748 A1 | 2/2012 | Weiman |
| 2012/0059472 A1 | 3/2012 | Weiman |
| 2012/0059474 A1 | 3/2012 | Weiman |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0221051 A1 | 8/2012 | Robinson |
| 2012/0226357 A1 | 9/2012 | Varela |
| 2012/0330422 A1 | 12/2012 | Weiman |
| 2013/0023993 A1 | 1/2013 | Weiman |
| 2013/0023994 A1 | 1/2013 | Glerum |
| 2013/0085572 A1 | 4/2013 | Glerum et al. |
| 2013/0103156 A1 | 4/2013 | Packer et al. |
| 2013/0116793 A1 | 5/2013 | Kloss |
| 2013/0144391 A1 | 6/2013 | Siegal et al. |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2014/0067071 A1 | 3/2014 | Weiman et al. |
| 2014/0148904 A1 | 5/2014 | Robinson |
| 2014/0163683 A1 | 6/2014 | Seifert et al. |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |
| 2014/0343678 A1 | 11/2014 | Suddaby et al. |
| 2015/0012097 A1 | 1/2015 | Ibarra et al. |

(56) References Cited

U.S. PATENT DOCUMENTS

| | | |
|---|---|---|
| 2015/0066145 A1 | 3/2015 | Rogers et al. |
| 2015/0100128 A1 | 4/2015 | Glerum et al. |
| 2015/0100130 A1 | 4/2015 | Perrow |
| 2015/0112438 A1 | 4/2015 | McLean |
| 2015/0173917 A1 | 6/2015 | Radcliffe et al. |
| 2015/0230931 A1 | 8/2015 | Greenhalgh |
| 2015/0351928 A1 | 12/2015 | Butler et al. |
| 2015/0374507 A1 | 12/2015 | Wolters et al. |
| 2016/0051377 A1 | 2/2016 | Weiman et al. |
| 2016/0089247 A1 | 3/2016 | Nichols et al. |
| 2016/0120660 A1 | 5/2016 | Melkent et al. |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 | 12/2016 | Faulhaber |
| 2017/0014244 A1 | 1/2017 | Seifert et al. |
| 2017/0056197 A1 | 3/2017 | Weiman et al. |
| 2017/0172756 A1 | 6/2017 | Faulhaber |
| 2017/0216036 A1 | 8/2017 | Cordaro |
| 2017/0224504 A1* | 8/2017 | Butler ............. A61F 2/447 |
| 2017/0224505 A1 | 8/2017 | Butler et al. |
| 2017/0246006 A1 | 8/2017 | Carnes et al. |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1 | 11/2017 | Robinson |
| 2017/0333199 A1 | 11/2017 | Sharifi-Mehr et al. |
| 2017/0333200 A1 | 11/2017 | Arnin |
| 2017/0348116 A1 | 12/2017 | Weiman |
| 2017/0367842 A1 | 12/2017 | Predick et al. |
| 2018/0014947 A1 | 1/2018 | Baynham |
| 2018/0042732 A1* | 2/2018 | Seifert ............. A61F 2/4455 |
| 2018/0049885 A1 | 2/2018 | Weiman et al. |
| 2018/0055652 A1* | 3/2018 | Davenport ......... A61F 2/447 |
| 2018/0185163 A1 | 7/2018 | Weiman et al. |
| 2018/0243107 A1 | 8/2018 | Foley et al. |
| 2018/0256359 A1 | 9/2018 | Greenhalgh |
| 2018/0303621 A1 | 10/2018 | Brotman et al. |
| 2018/0318101 A1 | 11/2018 | Engstrom |
| 2018/0325693 A1 | 11/2018 | Weiman et al. |
| 2018/0360616 A1 | 12/2018 | Luu |
| 2019/0021871 A1 | 1/2019 | Baynham |
| 2019/0133779 A1* | 5/2019 | McLaughlin ........ A61F 2/4425 |
| 2019/0133784 A1 | 5/2019 | Gunn et al. |
| 2019/0201210 A1 | 7/2019 | Besaw et al. |
| 2019/0254836 A1 | 8/2019 | Cowan et al. |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1* | 10/2019 | Faulhaber .......... A61F 2/4611 |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0129307 A1 | 4/2020 | Hunziker et al. |
| 2020/0360153 A1 | 11/2020 | Weiman et al. |
| 2021/0015627 A1 | 1/2021 | Weiman et al. |
| 2021/0045891 A1 | 2/2021 | Rogers et al. |
| 2021/0045892 A1 | 2/2021 | Rogers et al. |
| 2021/0113349 A1 | 4/2021 | Weiman et al. |
| 2021/0137699 A1 | 5/2021 | Jang et al. |
| 2021/0259849 A1 | 8/2021 | Robinson et al. |
| 2021/0322181 A1 | 10/2021 | Predick |
| 2022/0133495 A1 | 5/2022 | Glerum et al. |
| 2022/0304823 A1 | 9/2022 | Melchor |
| 2022/0387184 A1 | 12/2022 | Josse et al. |

FOREIGN PATENT DOCUMENTS

| | | |
|---|---|---|
| DE | 94 07 806 U1 | 7/1994 |
| DE | 20314708 U1 | 11/2003 |
| EP | 0 880 950 A1 | 12/1998 |
| EP | 1 925 272 A1 | 5/2008 |
| EP | 2 777 633 A2 | 9/2014 |
| EP | 3 031 424 A1 | 6/2016 |
| EP | 3 245 982 | 11/2017 |
| EP | 3 479 799 A1 | 5/2019 |
| FR | 2717068 A1 | 4/1996 |
| FR | 2727003 B1 | 4/1997 |
| FR | 2894130 A1 | 6/2007 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-00/44319 A1 | 8/2000 |
| WO | WO-02/44319 A2 | 6/2002 |
| WO | WO-2004/052245 | 6/2004 |
| WO | WO-2005/009299 A1 | 2/2005 |
| WO | WO-2006/102485 A2 | 9/2006 |
| WO | WO-2006/105437 A2 | 10/2006 |
| WO | WO-2009/124269 A1 | 10/2009 |
| WO | WO-2010/148112 | 12/2010 |
| WO | WO-2012/121726 A1 | 9/2012 |
| WO | WO-2014/134590 A1 | 9/2014 |
| WO | WO-2014/165319 A1 | 10/2014 |
| WO | WO-2015/009793 A1 | 1/2015 |
| WO | WO-2015/063721 A1 | 5/2015 |
| WO | WO-2015/085111 A1 | 6/2015 |
| WO | WO-2016/051095 A1 | 4/2016 |
| WO | WO-2016/077610 A1 | 5/2016 |
| WO | WO-2016/127139 A1 | 8/2016 |
| WO | WO-2017/027277 A1 | 2/2017 |
| WO | WO-2017/027873 A1 | 2/2017 |
| WO | WO-2017/066463 A1 | 4/2017 |
| WO | WO-2017/106614 A1 | 6/2017 |
| WO | WO-2018/049227 A1 | 3/2018 |
| WO | WO-2018/200507 A1 | 11/2018 |
| WO | WO-2018/200530 A1 | 11/2018 |
| WO | WO-2019/014139 A1 | 1/2019 |
| WO | WO-2019/126213 A1 | 6/2019 |
| WO | WO-2019/241687 A1 | 12/2019 |
| WO | WO-2021/030645 A1 | 2/2021 |

OTHER PUBLICATIONS

Extended European Search Report for European Application No. 14159101.6, dated Jun. 18, 2014, 5 pages.

Extended European Search Report for European Application No. 16169890.7, dated Oct. 21, 2016, 7 pages.

Foreign Action other than Search Report on EP 06740268.5 dated Jan. 2, 2020, 4 pages.

Foreign Action other than Search Report on PCT PCT/US2018/029120 dated Nov. 7, 2019, 9 pages.

Foreign Action other than Search Report on PCT PCT/US2018/029149 dated Nov. 7, 2019, 8 pages.

Foreign Action other than Search Report on PCT PCT/US2018/041306 dated Jan. 23, 2020, 6 pages.

Foreign Search Report on PCT PCT/US2019/037275 dated Sep. 24, 2019, 12 pages.

International Preliminary Report on Patentability for Application No. PCT/US06/12060 dated Sep. 30, 2007, 3 pages.

International Search Report and Written Opinion for International Application No. PCT/US2006/012060, dated Apr. 5, 2007, 4 pages.

International Search Report and Written Opinion for International Application No. PCT/US2012/057324, dated Dec. 20, 2012, 10 pages.

International Search Report for Application No. PCT/US06/12060, dated Apr. 5, 2007, 1 page.

International Search Report for International Application No. PCT/US2018/029120, dated Jun. 28, 2018, 17 pages.

International Search Report for International Application No. PCT/US2018/029149, dated Jun. 25, 2018, 13 pages.

Search Report for International Application No. PCT/US2018/041306, dated Sep. 28, 2018, 12 pages.

Written Opinion of the International Searching Authority for Application No. PCT/US06/12060, dated Apr. 5, 2007, 3 pages.

Foreign Search Report on PCT PCT/US2021/026606 dated Jul. 15, 2021, 20 pages.

(56) References Cited

OTHER PUBLICATIONS

Final Office Action on U.S. Appl. No. 16/009,616 dated Jul. 6, 2021.
International Search Report and Written Opinion in PCT PCT/US2021/030261 dated Aug. 31, 2021 (18 pages).
International Search Report and Written Opinion in PCT/US2021/031596 dated Sep. 28, 2021 (12 pages).
International Search Report and Written Opinion in PCT/US2021/033832 dated Sep. 17, 2021.
International Search Report and Written Opinion on PCT/US2020/036809 dated Sep. 14, 2020, 12 pages.
International Search Report and Written Opinion received for Life Spine, Inc., for PCT app. No. PCT/US2021026610 dated Jul. 20, 2021, 18 pages.
International Search Report on PCT/US2020/037020, dated Sep. 29, 2020, 20 pages.
Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.
Schizas, C., "Spinal Fusion: Techniques Results and Limitations." European Cells and Materials. 2005, vol. 10, Suppl. 3, p. 1.
"MectaLIF Oblique & Posterior Intervertebral Body Fusion Device." Brochure. 2004, Medacta International, San Pietro, Switzerland.
"Webster's II New College Dictionary." Excerpts. 2005, Houghton Mifflin Co., p. 992.
"Wedge." Encyclopedia Brittanica. Aug. 14, 2008. britannica.com/print/article/638734.
Kambin, P., et al., "Arthroscopic Discectomy of the Lumbar Spine." Clinical Orthopaedics and Related Research. Apr. 1997, No. 337, pp. 49-57.
Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.
Kim, Y, et al., "Clinical Applications of the Tubular Retractor on Spinal Disorders." Journal of Korean Neurosurgery, Nov. 2007, No. 42, pp. 244-250.
Moore, J., et al, "Mechanics Map—Wedges." Aug. 20, 2022, mechanicsmap.psu.edu/websites/7_friction/7-3_wedges/wedges.
Peltier, L. "Orthopedics: A History and Iconography" 1993, Norman Publishing, San Francisco, CA.
Sasso, R., et al., "Anterior Lumbar Interbody Fusion." Surgical Management of Low Back Pain. 2009, Chapter 10, pp. 87-95.
Tsuang, Y., et al., "Comparison of cage application modality in posterior lumbar interbody fusion with posterior instrumentation—A finite element study." Medical Engineering & Physics 31. 2009, pp. 565-570.
Virk, S., et al. "History of Spinal Fusion: Where We Came from and Where We Are Going." Current Concepts in Spinal Fusion. HSS Journal, 2020, No. 16, pp. 137-142.
Xiao, Y, et al., "Unilateral Transforaminal Lumbar Interbody Fusion: a Review of the Technique, Indications and Graft Materials." The Journal of International Medical Research. 2009, No. 37, pp. 908-917.
International Search Report and Written Opinion in PCT/US2022/053230 dated May 3, 2023 (18 pages).

\* cited by examiner

EXPANDABLE IMPLANT ASSEMBLY

BACKGROUND

The present disclosure generally relates to implants. More specifically, the present application relates to expandable implants and devices, including spinal interbody and intravertebral body devices, and vertebral interbody and intravertebral devices that are expandable after spinal placement thereof.

Many people contend with spine or other issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posterolaterally.

SUMMARY

In some embodiments, an implant includes an upper support that includes an upper plate configured to receive a first anchoring member and a lower support that includes a lower plate configured to receive a second anchoring member. The implant also includes a control member that includes a head and a shaft and configured to control relative movement between the upper support and the lower support, a front portion configured engage the upper support and the lower support and further configured to receive the head of the control member, and a rear portion configured engage the upper support and the lower support and further configured to engage a portion of the shaft, wherein manipulation of the control member causes the front portion to move relative to the rear portion, such that the upper support moves relative to the lower support.

In some embodiments, a method of installing an implant includes inserting the implant into a desired location. The implant includes an upper support that includes an upper plate configured to receive a first anchoring member, a lower support that includes a lower plate configured to receive a second anchoring member, and a control assembly including a control member, a front member, and a rear member, wherein the control assembly is configured to control relative movement between the upper support and the lower support. The method further includes manipulation the control member to cause relative sliding movement between the front member and both the upper support and the lower support, and the rear member and both the upper support and the lower support, to expand the implant to a desired height, and securing the first and second anchoring members into adjacent portions of bone to secure the implant into the desired location.

In some embodiments, an implant includes an upper support configured to engage a first portion of bone. The upper support includes an upper plate at a first end of the upper support configured to secure the upper support to the first portion of bone. The implant also includes a lower support configured to engage a second portion of bone. The lower support includes a lower plate at a first end of the lower support configured to secure the lower support to the second portion of bone. The implant includes a control assembly configured to control relative movement between the upper support and the lower support. The control assembly includes a front portion configured to engage the upper support at the first end of the upper support, a rear portion configured to engage the upper support at a second end of the upper support, the second end being opposite the first end, and a control member adjustably engaging the front portion and the rear portion.

BRIEF DESCRIPTION OF THE FIGURES

The features of the subject matter disclosed herein will be better understood by reference to the accompanying drawings which illustrate the subject matter disclosed herein, wherein.

Figure 1:
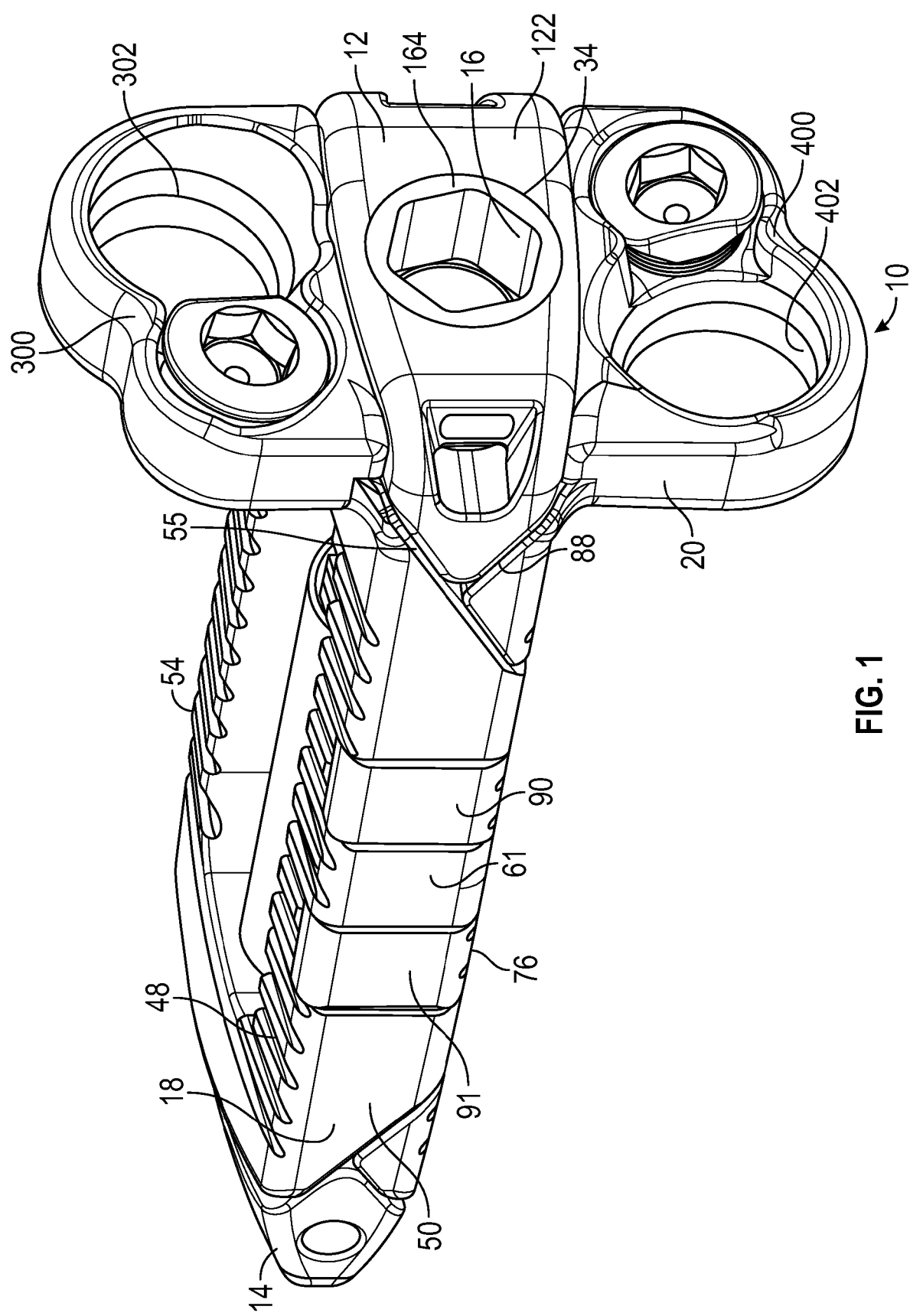
FIG. 1 is a perspective view of an implant in a collapsed position according to an example embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

The present disclosure relates to expandable and/or dynamic implants. In an example embodiment, the implant may be an interbody (between adjacent vertebrae), intravertebral-body (inside the vertebrae) and/or spinal stabilization device that may or may not be used as an interbody fusion cage or device, interbody/intravertebral body stabilization device and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (expandable and/or expandable and retractable) interbody/intravertebral body devices that are usable in a spinal column or other areas of a human.

Various embodiments disclosed herein are directed to expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to FIGS. 1-10, an expandable implant 10 is shown according to an exemplary embodiment. The implant 10 is usable, for example, between and/or within vertebral bodies of the spine. It should be understood that the implant 10 may in some embodiments be usable in other portions of the body in addition to the spine, and all such applications are to be understood to be within the scope of the present disclosure.

According to an exemplary embodiment, the implant 10 includes a first, or front component 12 (e.g., a first wedge member), a second, or rear component 14 (e.g., a second wedge member), and a third, intermediate, or control member 16, which collectively form a control assembly that extends along a longitudinal axis of the implant 10. A first, or upper support 18 (e.g., an upper plate, support member, assembly, etc.) and a second, or lower support 20 (e.g., a lower plate, support member, assembly), are coupled to the body assembly and extend generally between the front component 12 and rear component 14. In certain embodiments, the upper support 18 may be identical to the lower support 20, which may reduce manufacturing costs of the implant 10.

According to an exemplary embodiment, the upper and lower supports 18, 20 define a height of the implant 10 (e.g., a support height defined by the upper and lower grooved/toothed surfaces of the implant), wherein the height of the implant 10 is the vertical distance between an outer or top surface 48 of upper support 18 and outer or lower surface 76 of lower support 20.

In some embodiments, the top surface 48 of the upper support 18 is substantially parallel to the lower surface 76 of the lower support 20. In these embodiments, the height of the implant 10 is substantially constant throughout the implant 10. However, in other embodiments, the top surface 48 of the upper support 18 and the lower surface 76 of the lower support 20 are not parallel. For example, the top surface 48 of the upper support 18 and the lower surface 76 of the lower support 20 may form an angle, such that the height of the implant 10 is not consistent throughout, as will be discussed further herein.

Figure 13:
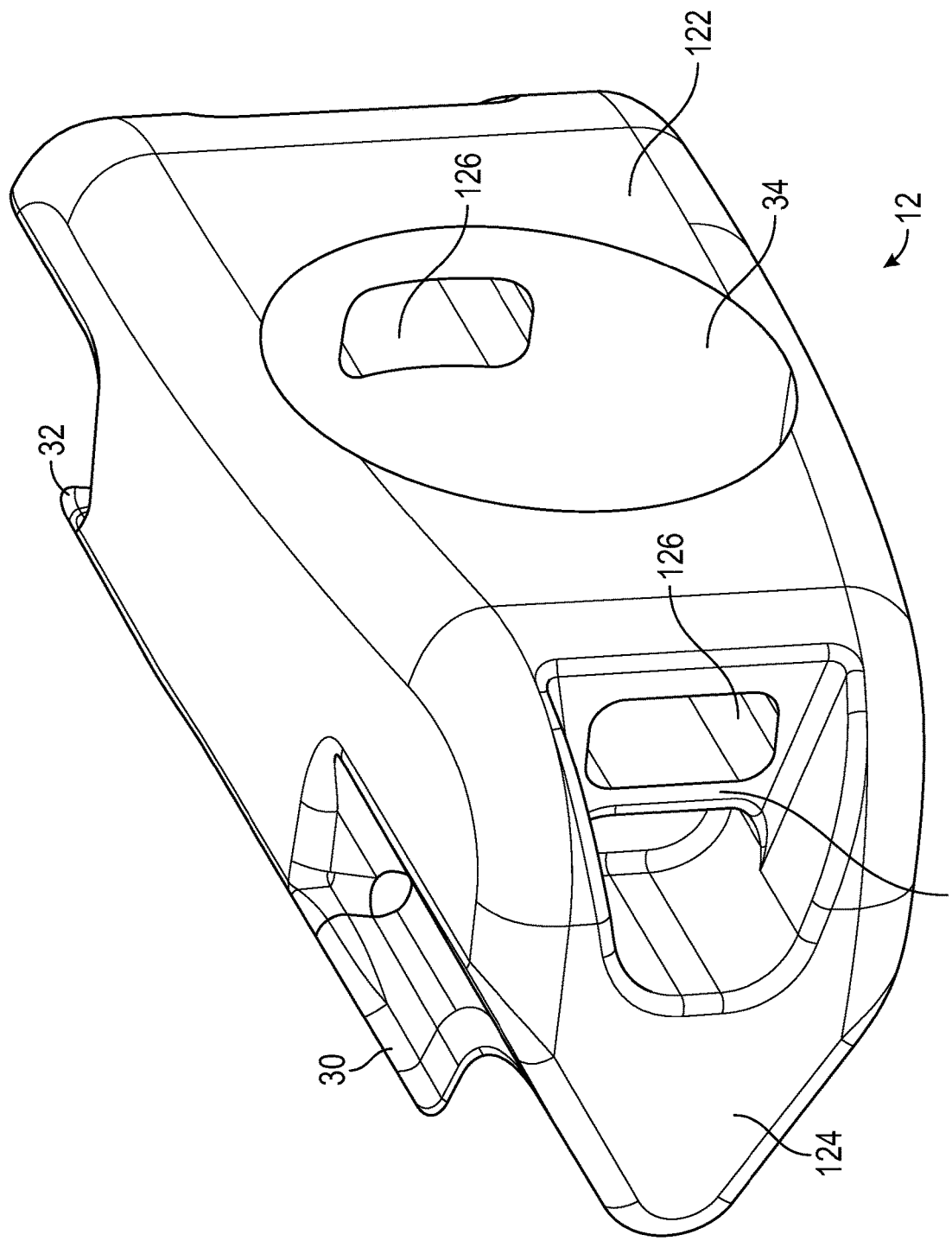
FIG. 13 is a perspective view of a front component of the implant of FIG. 1 according an example embodiment.
Figure 14:
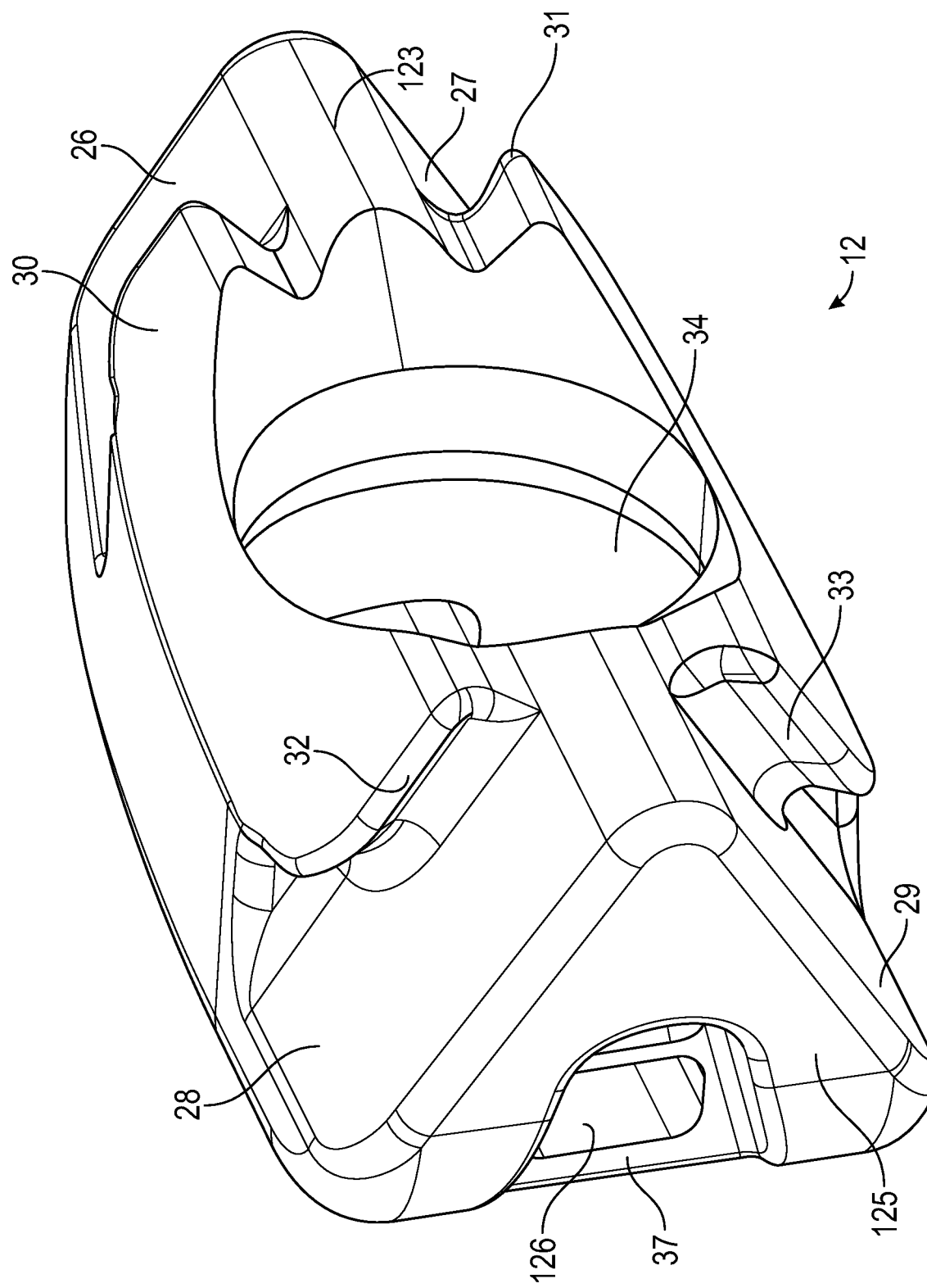
FIG. 14 is another perspective view of the front component of the implant of FIG. 1 according an example embodiment.
Figure 15:
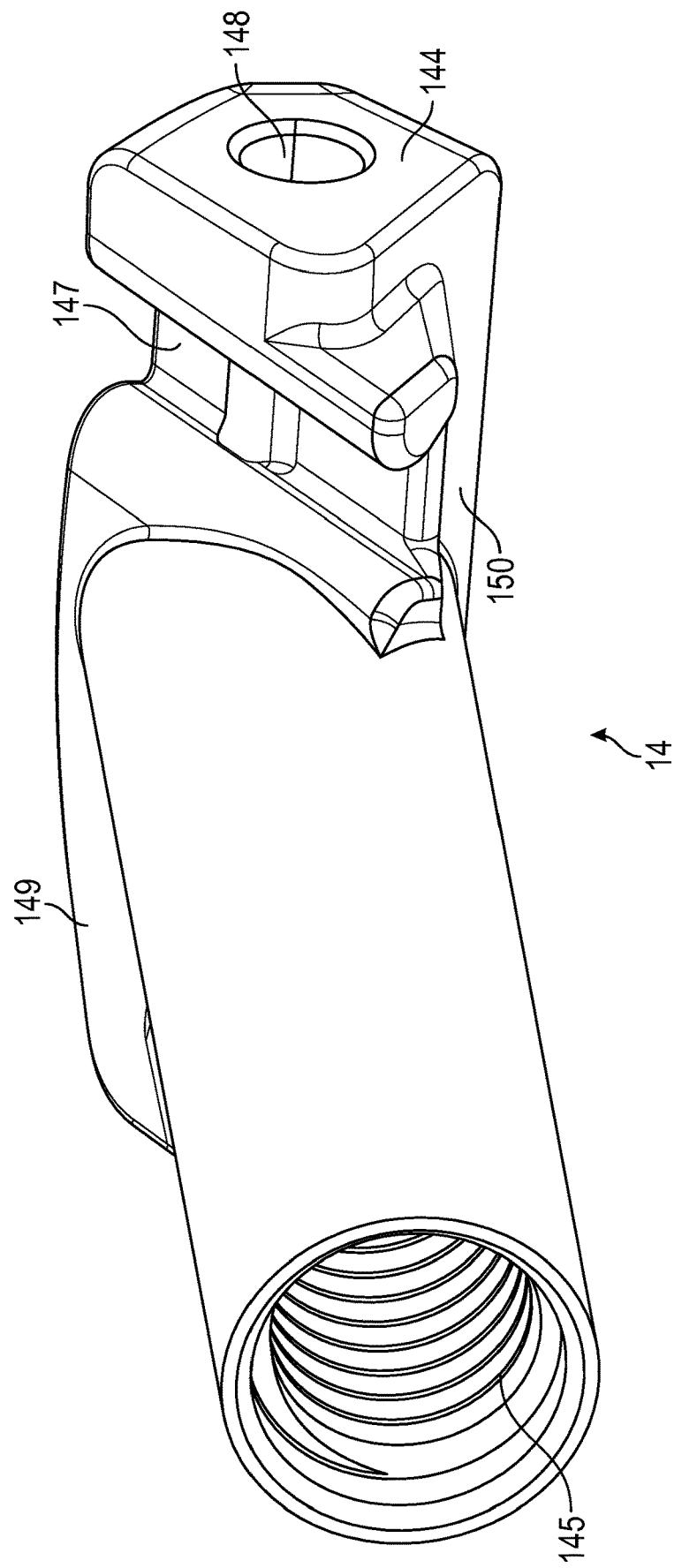
FIG. 15 is a perspective view of a rear component of the implant of FIG. 1 according an example embodiment.

In some embodiments, such as the embodiments shown in FIGS. 13 and 14, the front component 12 includes a front portion 122, a rear portion 123 opposite the front portion 122, a first side portion 124, and a second side portion 125 opposite the first side portion 124. The front component 12 also includes a first ramped surface 26 and a second ramped surface 27 proximate the first side portion 124. The front component 12 also includes a third ramped surface 28 and fourth ramped surface 29 proximate the second side portion 125. Further, the front component 12 includes a first projection 30 proximate the first ramped surface 26, a second projection 31 proximate the second ramped surface 27, a third projection 32 proximate the third ramped surface 28, and a fourth projection 33 proximate the fourth ramped surface 29.

Figure 2:
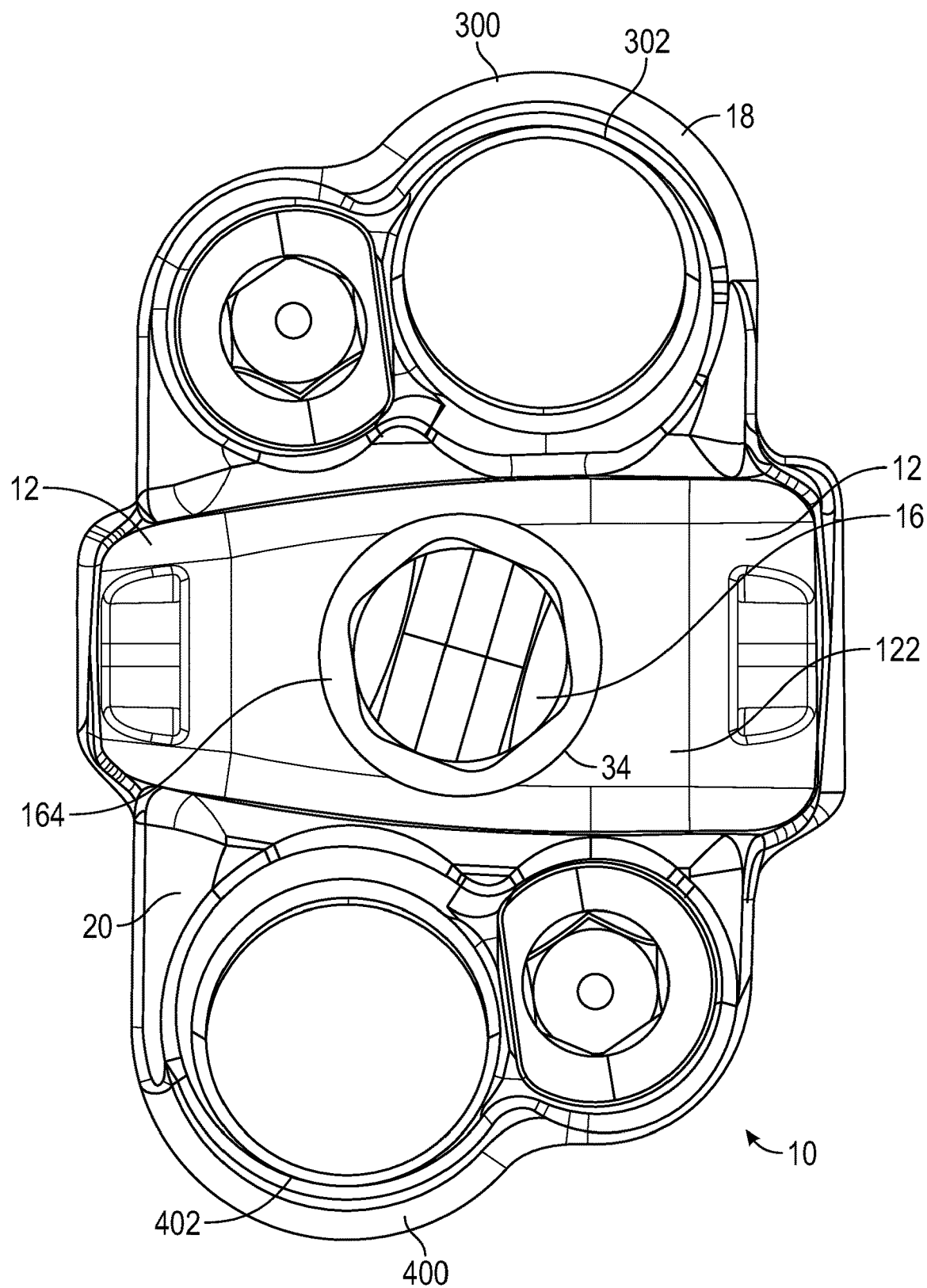
FIG. 2 is a front view of the implant of FIG. 1 in a collapsed position according to an example embodiment.

In certain embodiments, the front portion 122 of the front component 12 may have an angular profile as shown in FIG. 2. For example, the height of the front portion 122 (i.e., the distance between surface of the front portion 122 that engages the upper support 18 and the surface of the front portion 122 that engages the lower support 20) may be greater proximate the second side portion 125 (see FIG. 14) than the height of the front portion 122 proximate the first side portion 124 (see FIG. 13).

In some embodiments, the first ramped surface 26 and the third ramped surface 28 are angled in an upwards direction towards the top surface 48 of the upper support 18. Conversely, the second ramped surface 27 and fourth ramped surface 29 are angled in a downwards direction towards the lower surface 76 of the lower support 20. The ramped surfaces 26, 27, 28, 29 and the projections 30, 31, 32, 33 facilitate controlled sliding movement of the upper support 18 and the lower support 20, as will be discussed further herein.

In some embodiments, the front component 12 may include a control bore 34 configured to receive the control member 16, such that the control bore 34 extends from the front portion 122 through the rear portion 123. In some embodiments, the control bore 34 may be threaded. In other embodiments, such as the embodiment shown in FIGS. 13 and 14, the control bore 34 may be unthreaded. Further, the front component 12 may include a first installation tool interface 35 proximate the first side portion 124 and a second installation tool interface 37 proximate the second side portion 125. The first and second tool interface 35, 37 may be utilized with an installation tool to assist a medical practitioner or other user in inserting the implant 10 into a patient, as will be discussed further herein.

Figure 11:
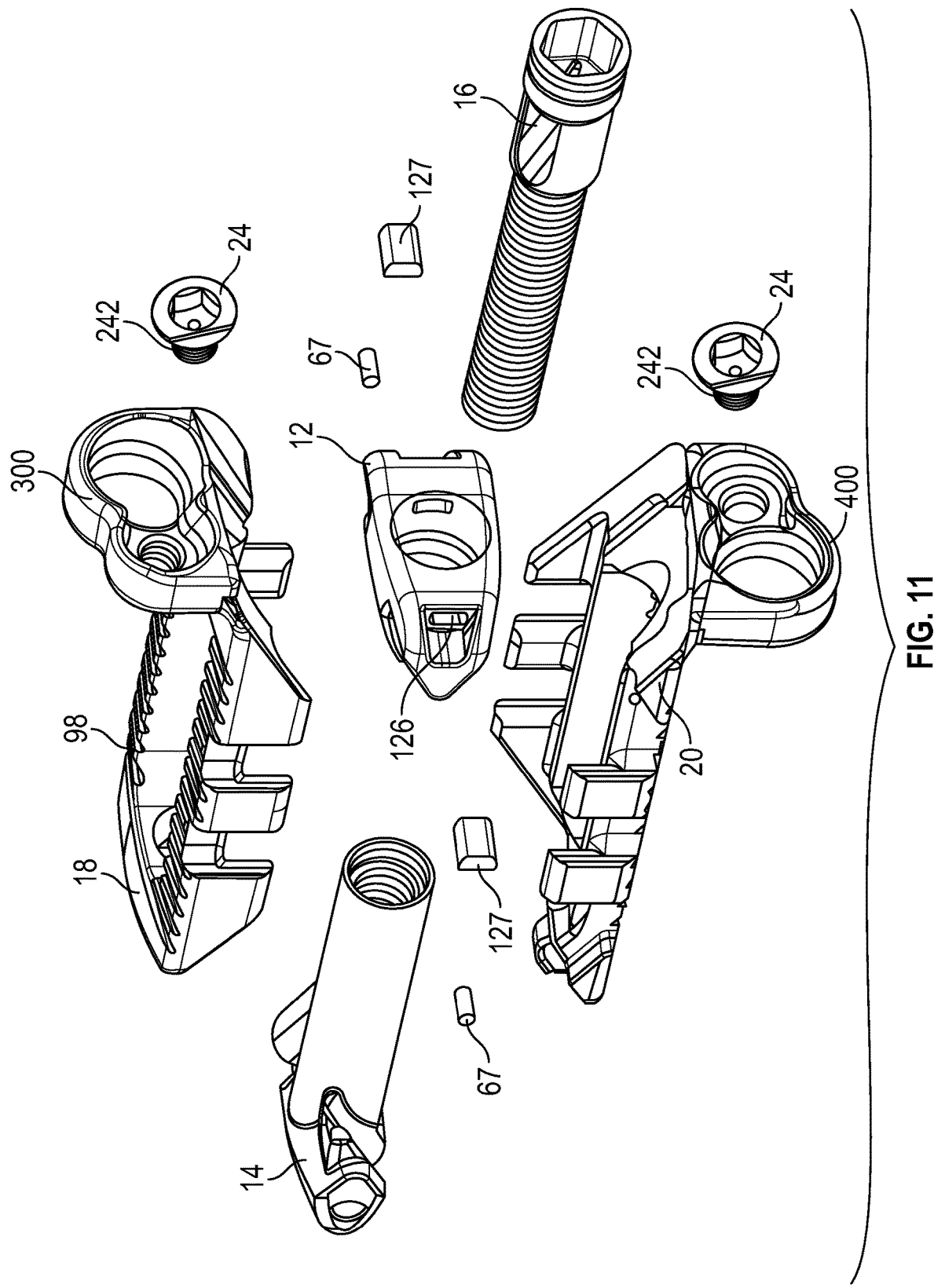
FIG. 11 is an exploded view of the implant of FIG. 1 according an example embodiment.
Figure 12:
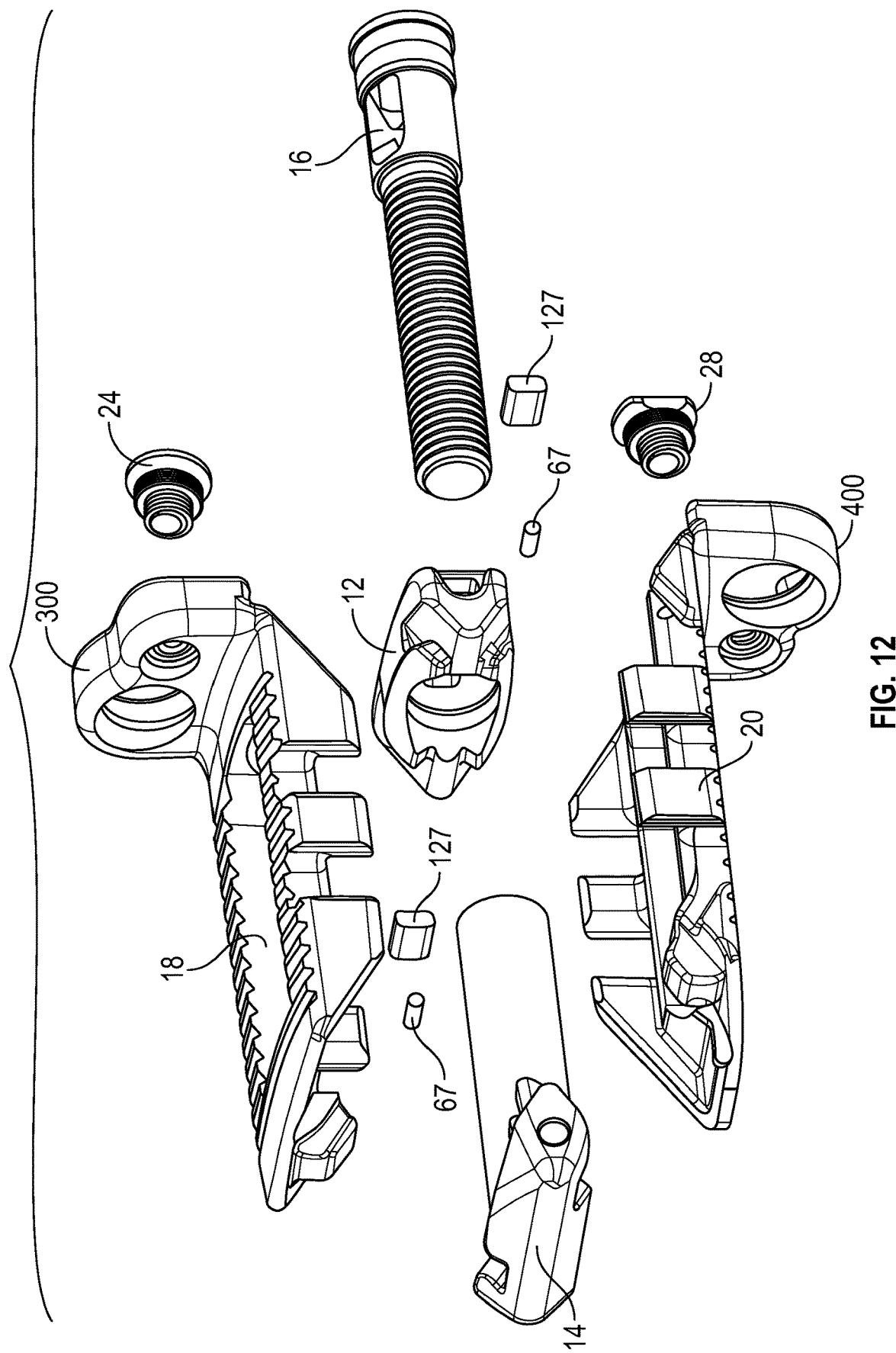
FIG. 12 is another exploded view of the implant of FIG. 1 according an example embodiment.

Further, the front component 12 may include a wedge slot 126 on the first side portion 124 and a wedge slot 126 on the second side portion 125. As shown in FIGS. 12 and 13, the wedge slots 126 may span from the first side portion 124 into the control bore 34 or from the second side portion 125 into the control bore 34. The wedge slot 126 is configured to receive a portion of a retention wedge 127 (see FIG. 11).

Figure 3:
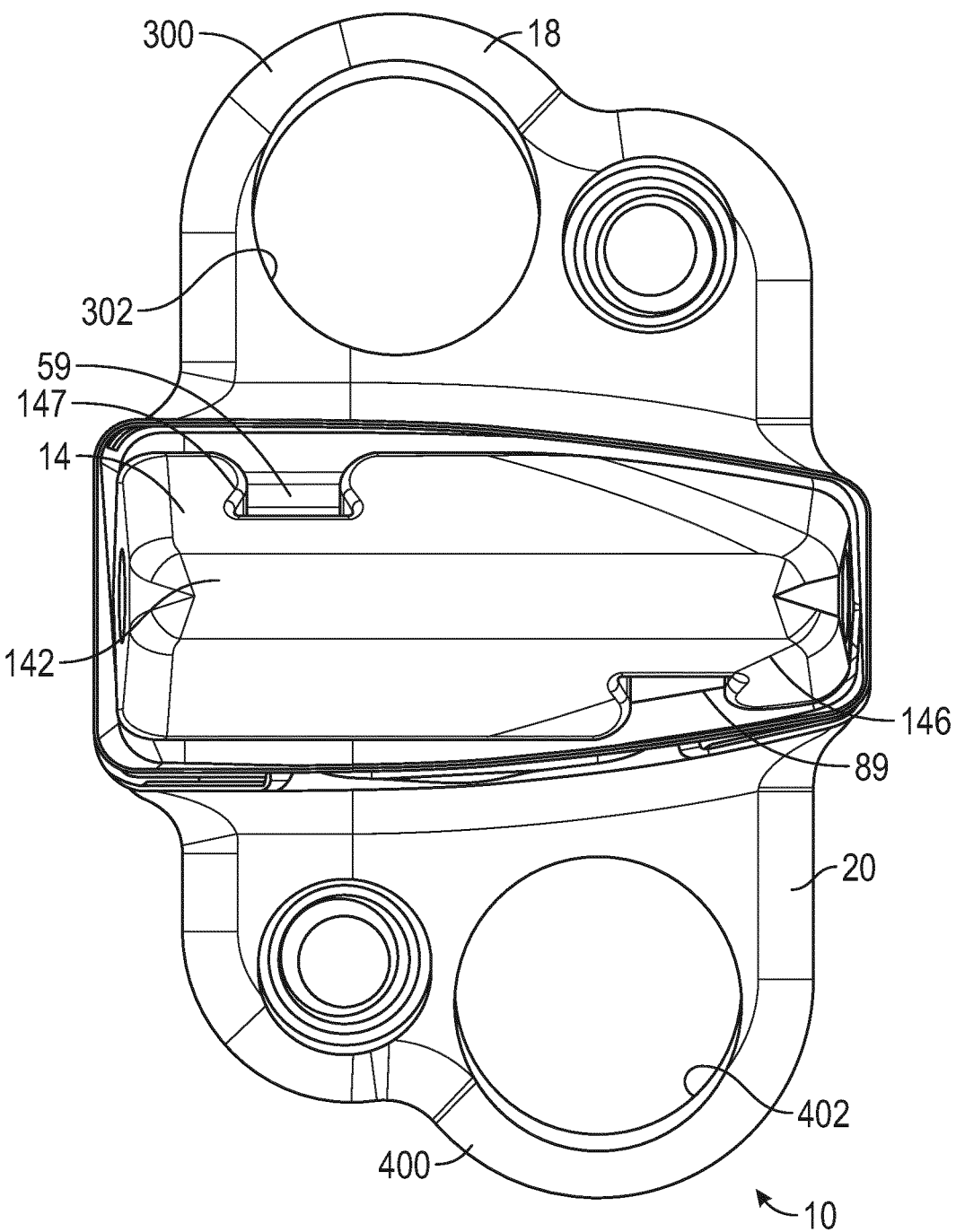
FIG. 3 is a rear view of the implant of FIG. 1 in a collapsed position according to an example embodiment.

In some embodiments, such as the embodiment shown in FIG. 3, the rear component 14 includes a rear nose 142, a threaded bore 145 positioned opposite the rear nose 142, a first side portion 143, and a second side portion 144 opposite the first side portion 143. The rear nose 142 also includes an upper ramp 149 and a lower ramp 150. Further, in some embodiments, the rear component 14 includes a first guide groove 146 proximate the first side portion 143 and a second guide groove 147 proximate the second side portion 144. In some embodiments, as viewed from the front, the first guide groove 146 is generally angled downwards towards the lower surface 76 of the lower support 20, and the second guide groove 147 is generally angled upwards towards the top surface 48 of the upper support 18. The first guide groove 146 and the second guide groove 147 may facilitate controlled sliding movement of the upper support 18 and the lower support 20, as will be discussed further herein.

Figure 16:
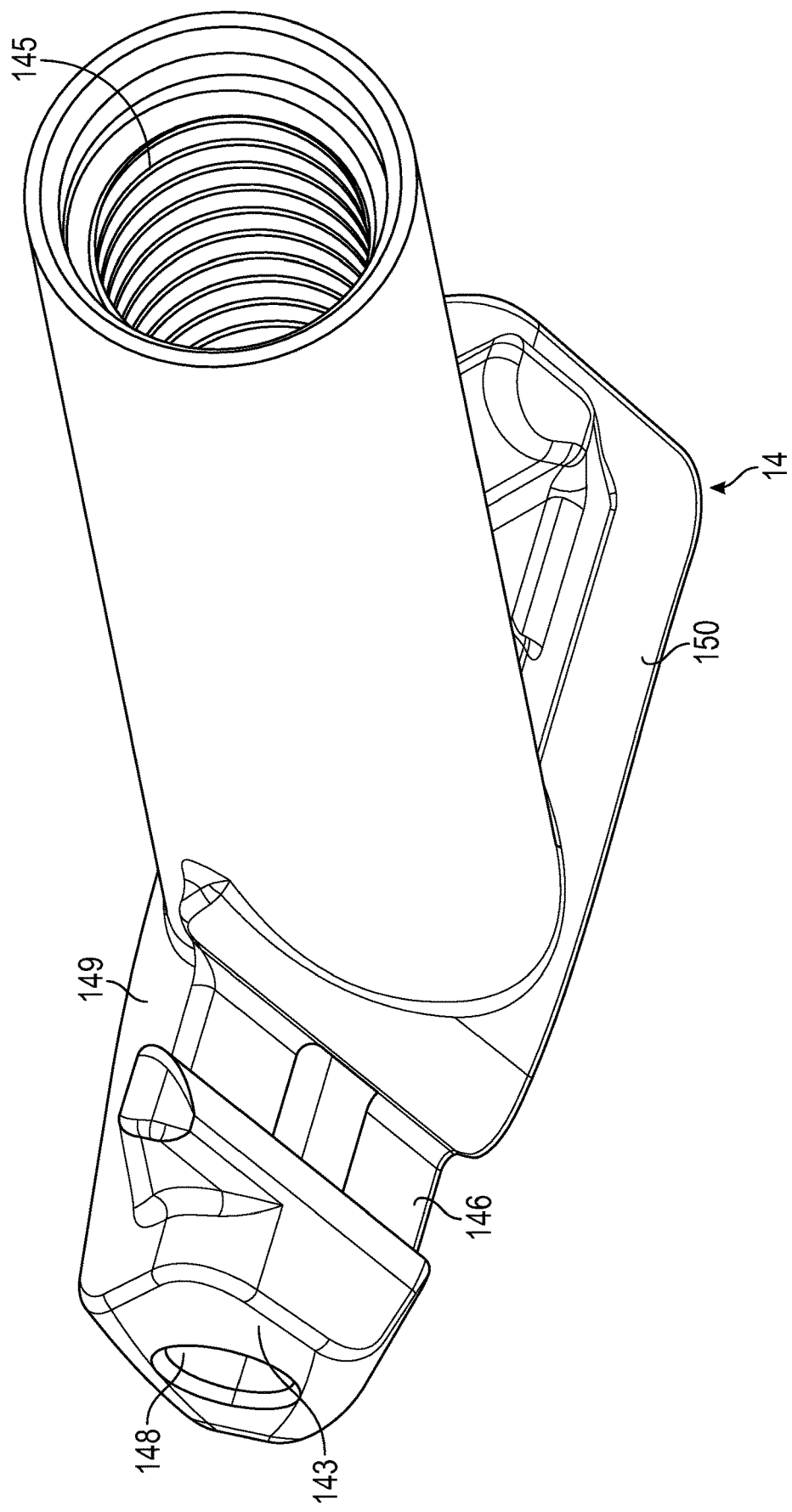
FIG. 16 is another perspective view of the rear component of the implant of FIG. 1 according an example embodiment.
Figure 17:
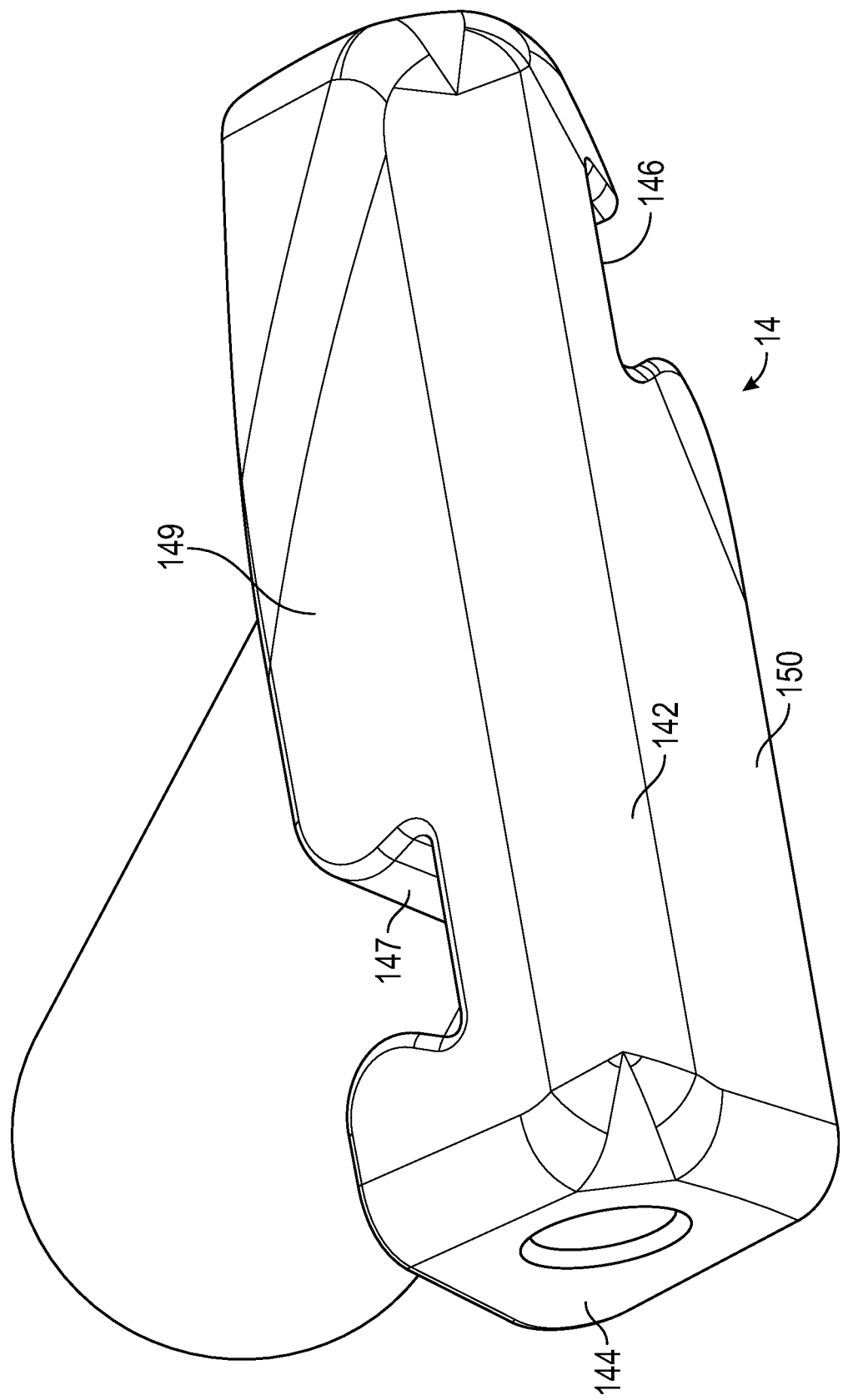
FIG. 17 is another perspective view of the rear component of the implant of FIG. 1 according an example embodiment.

In some embodiments, the rear nose 142 of the rear component 14 may be generally wedge-shaped. In further embodiments, the rear nose 142 may also include a nose at either the first side portion 143 or second side portion 144. For example, as shown in FIG. 16, the generally wedge-shaped rear nose 142 of the rear component 14 also includes a nose proximate the first side portion 143 of the rear component 14. In some embodiments, having a nose, such as the nose on the first proximate side 143 of the rear component 14, may facilitate inserting the implant 10 into a patient, as will be discussed further herein. Further, in some embodiments, the rear component 14 may have a through whole 148 extending from the first side portion 143 to the second side portion 144.

Figure 18:
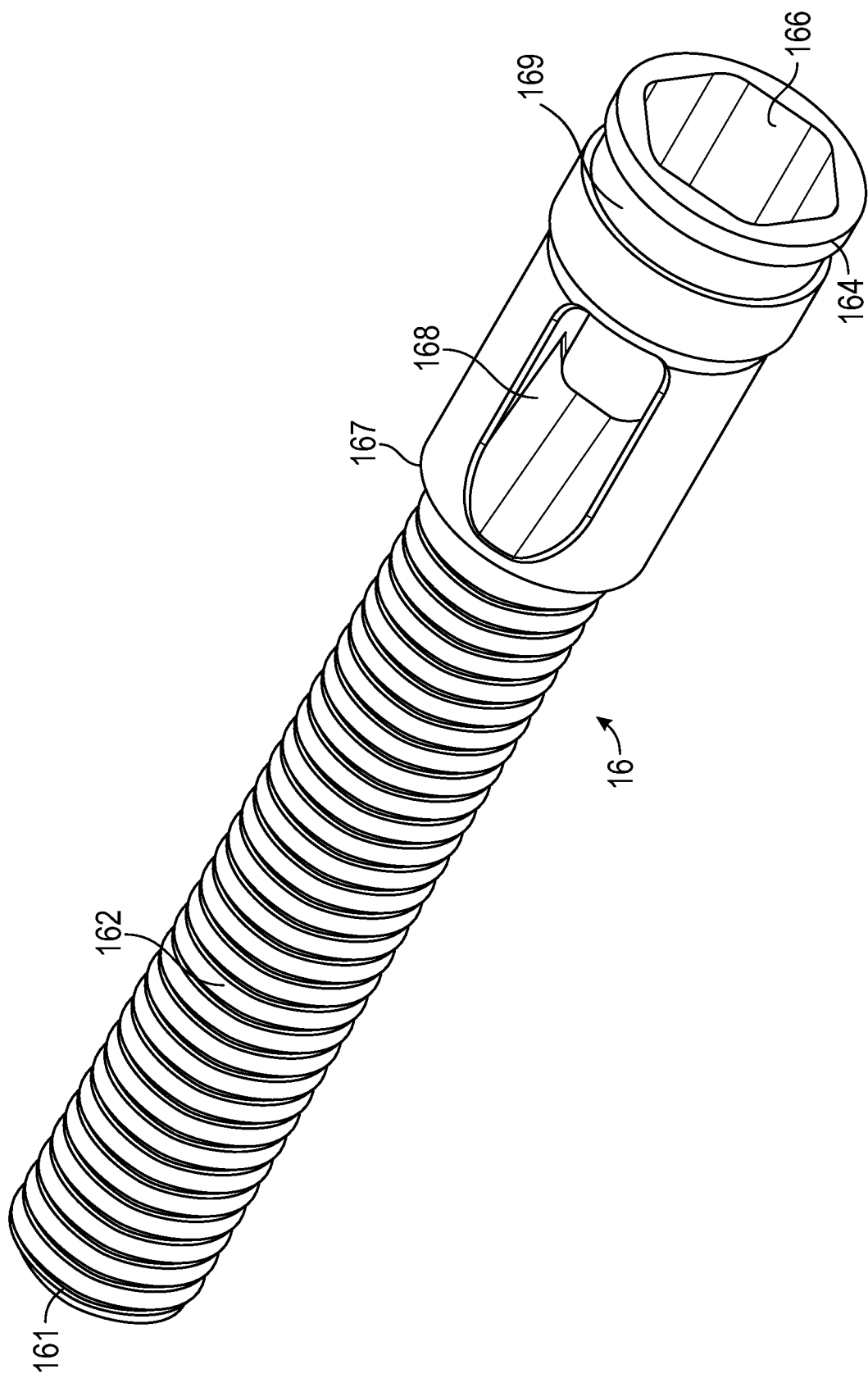
FIG. 18 is a perspective view of a control member of the implant of FIG. 1 according an example embodiment.

Referring now to FIG. 18, the control member 16 includes a tip 161 at a first end and a head 164 at a second end, opposite the first end. In some embodiments, the tip 161 may be flat. In some embodiments, the control member 16 also includes a threaded shaft 162 extending from the tip 161 to a shoulder 167. In other embodiments, the control member 16 may include a plurality of teeth or strips or other securing mechanisms that may be received by the rear component 14, as will be discussed further herein. The control member 16 also may include a through hole 168 that may facilitate implanting bone graft growth within the implant 10. Through hole 168 may be in communication with a tool port 166 to enable insertion of bone graft or other material into the interior of implant 10 via tool port 166. In some embodiments through hole 168 defines openings on opposing portions of control member 16. The control member 16 may also include a groove 169 near the head 164. The groove 169 may be configured to receive a portion of a retention wedge 127 in order to prevent back out of the control member 16.

In some embodiments, the tool port 166 is configured to receive a tool that may be used to manipulate the control member 16. For example, the tool port 166 may be configured to receive a hex head driver. While this example embodiment shows the tool port 166 as being a hex head socket, it should be appreciated that the tool port 166 can be designed to receive several different types of hand tools, including a slotted screwdriver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

Figure 19:
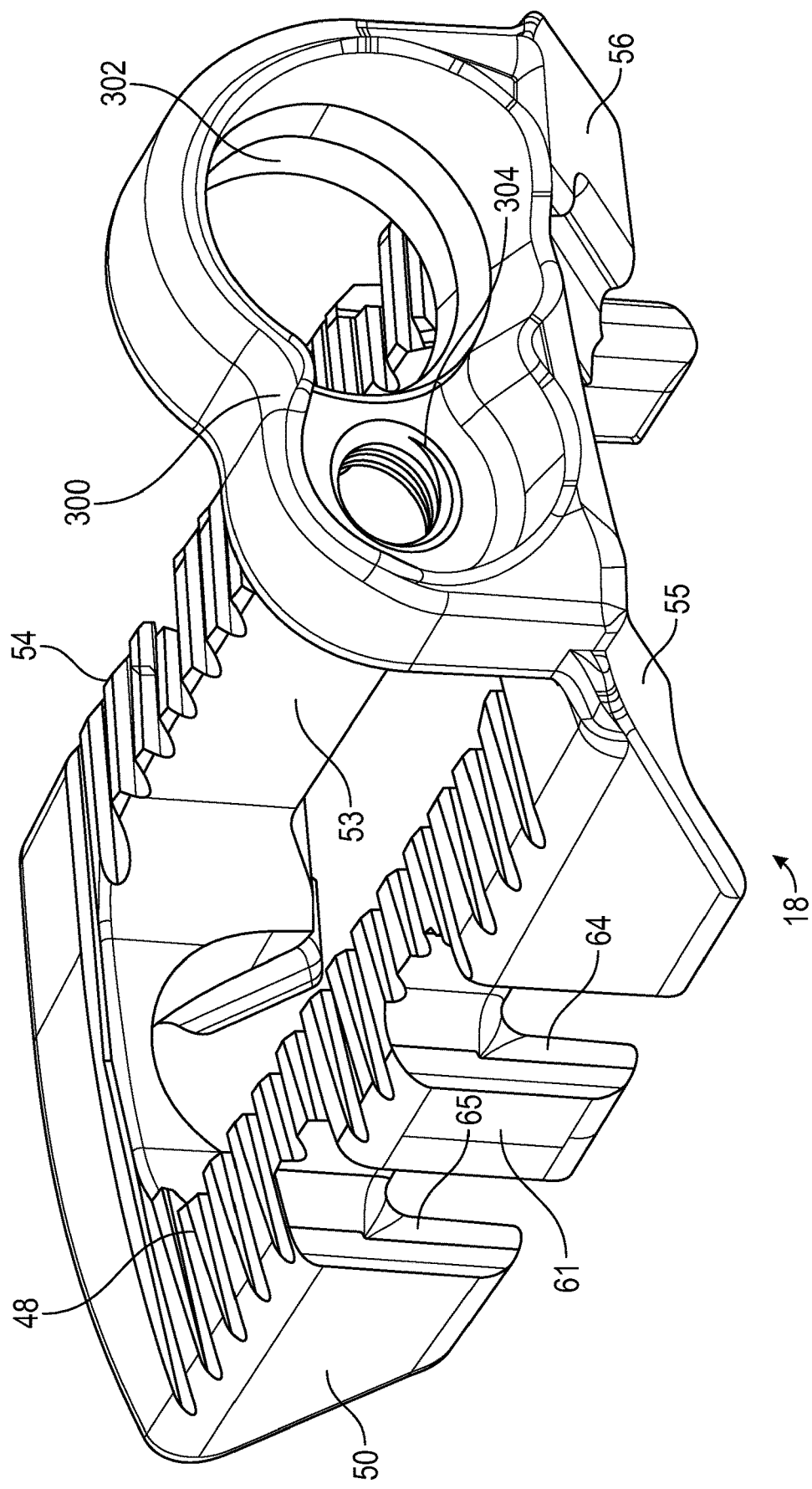
FIG. 19 is a perspective view of an upper support of the implant of FIG. 1 according an example embodiment.
Figure 20:
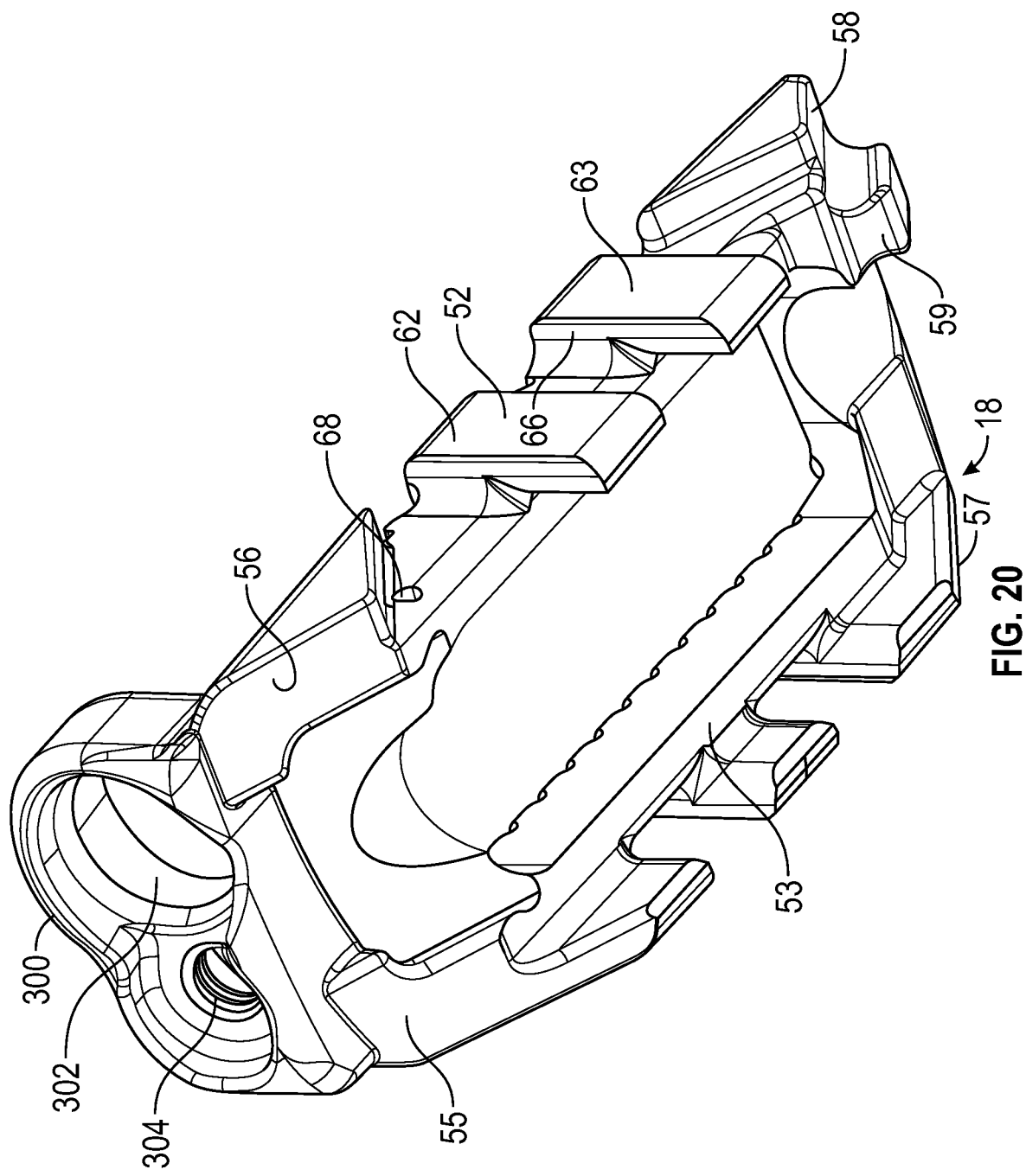
FIG. 20 is another perspective view of the upper support of the implant of FIG. 1 according an example embodiment.

Referring to FIGS. 19 and 20, the upper support 18 is shown according to an example embodiment. In this example embodiment, the upper support 18 includes a top surface 48, a front portion 49, a rear portion 51 opposite the front portion 49, a first side 50, and a second side 52 opposite the first side 50. In this example embodiment, the upper support 18 further includes a plurality of ridges 54 on the top surface 48. The series of ridges 54 may create a surface roughness that provides additional stability of the implant 10 once installed.

The upper support 18 further includes a first ramp 55, a second ramp 56, a third ramp 57, and a fourth ramp 58. The first ramp 55 and the second ramp 56 are proximate the front portion 49, and are configured to engage the first ramped surface 26 and the third ramped surface 28 of the front component 12. In some example embodiments, the first ramp 55 will slide along the first ramped surface 26 of the front component 12 and the second ramp 56 will slide along the third ramped surface 28 of the front component 12 as the implant 10 expands from a first position to a second position.

The upper support 18 further includes a third ramp 57 and a fourth ramp 58 proximate the rear portion 51 of the upper support 18. The third ramp 57 and the forth ramp 58 are configured to engage the upper ramp 149 of the rear component 14. In some example embodiments, the third ramp 57 and the fourth ramp 58 will slide along the upper ramp 149 of the rear component 14 as the implant 10 expands from a first position to a second position.

The upper support 18 may further includes a guide rail 59 proximate the rear portion 51. The guide rail 59 is configured to be received by the second guide groove 147 of the rear component 14. In some embodiments, the guide rail 59 will translate within the second guide groove 147 of the rear component as the implant 10 expands from a first position to a second position, as will be discussed further herein. In some embodiments, the guide rail 59 and the guide groove 147 may be dovetail shaped, as shown in FIG. 3. The dovetail shape may help keep the various components of the implant from undesirably shifting relative to one another.

Further, the upper support 18 may include a first side projection 61, a first side slot 64, and a second side slot 65 proximate the first side 50. The upper support 18 may also include a second side projection 62, a third side projection 63, and a third side slot 66 proximate the second side 52. Additionally, the upper support 18 may include a pin aperture 68 proximate the second side 52. The pin aperture 68 may be configured to receive a pin 67, as will be discussed further herein.

In some embodiments, the upper support 18 further includes an upper mounting plate 300 proximate the front portion 49. In this example embodiment, the upper mounting plate 300 is integrated into the upper support 18, such that the upper support 18 and upper mounting plate 300 are manufactured as one piece. For example, the upper support 18 and upper mounting plate 300 may be 3D printed as a single piece. The upper mounting plate 300 may include an unthreaded bore 302 configured to receive a first portion of an anchoring member, such as a bone screw 22 (see FIG. 23), as will be discussed further herein. Additionally, the upper mounting plate 300 may include a threaded bore 304 configured to receive a retention member 24 (see FIG. 23), as will be discussed further herein.

Figure 21:
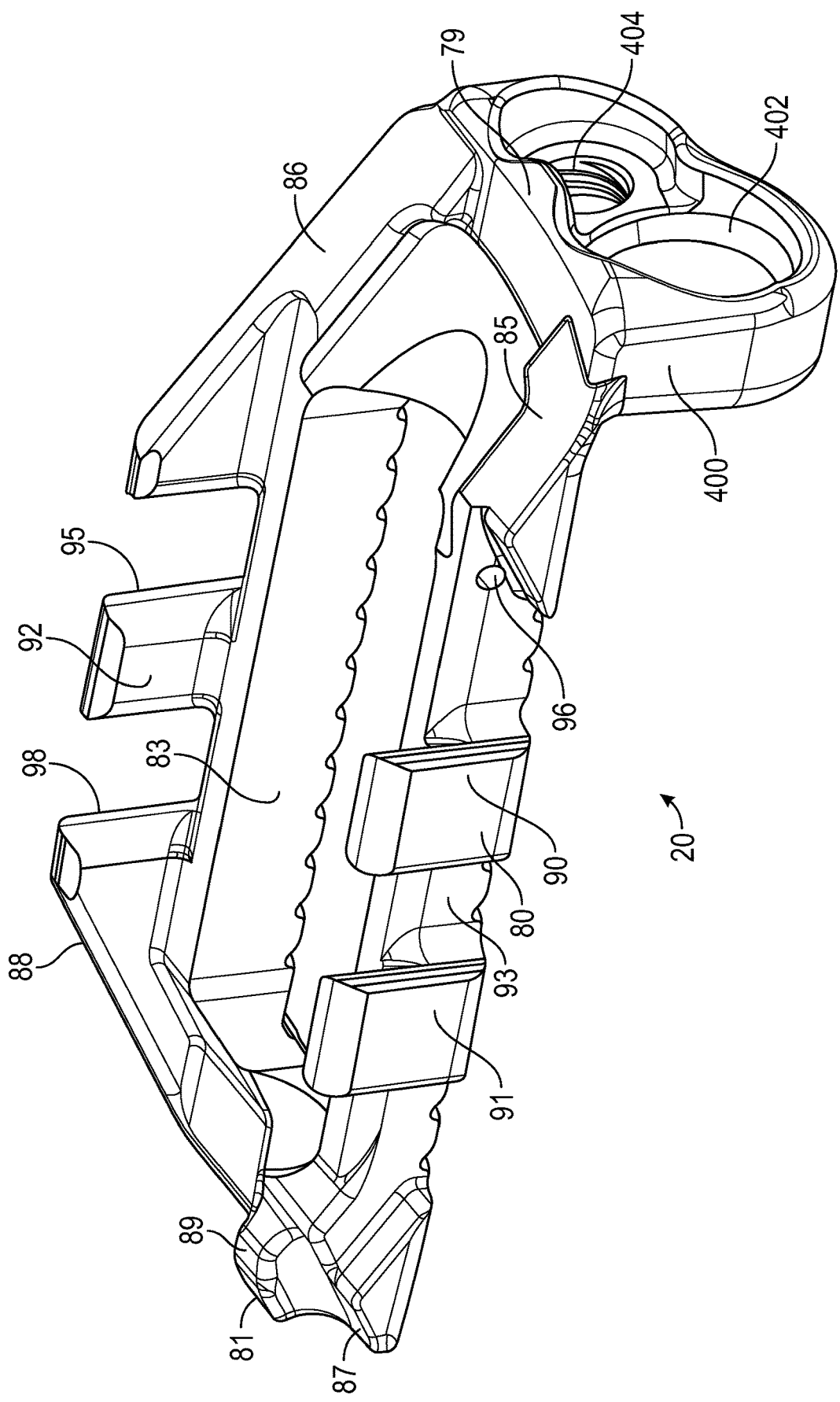
FIG. 21 is a perspective view of a lower support of the implant of FIG. 1 according an example embodiment.
Figure 22:
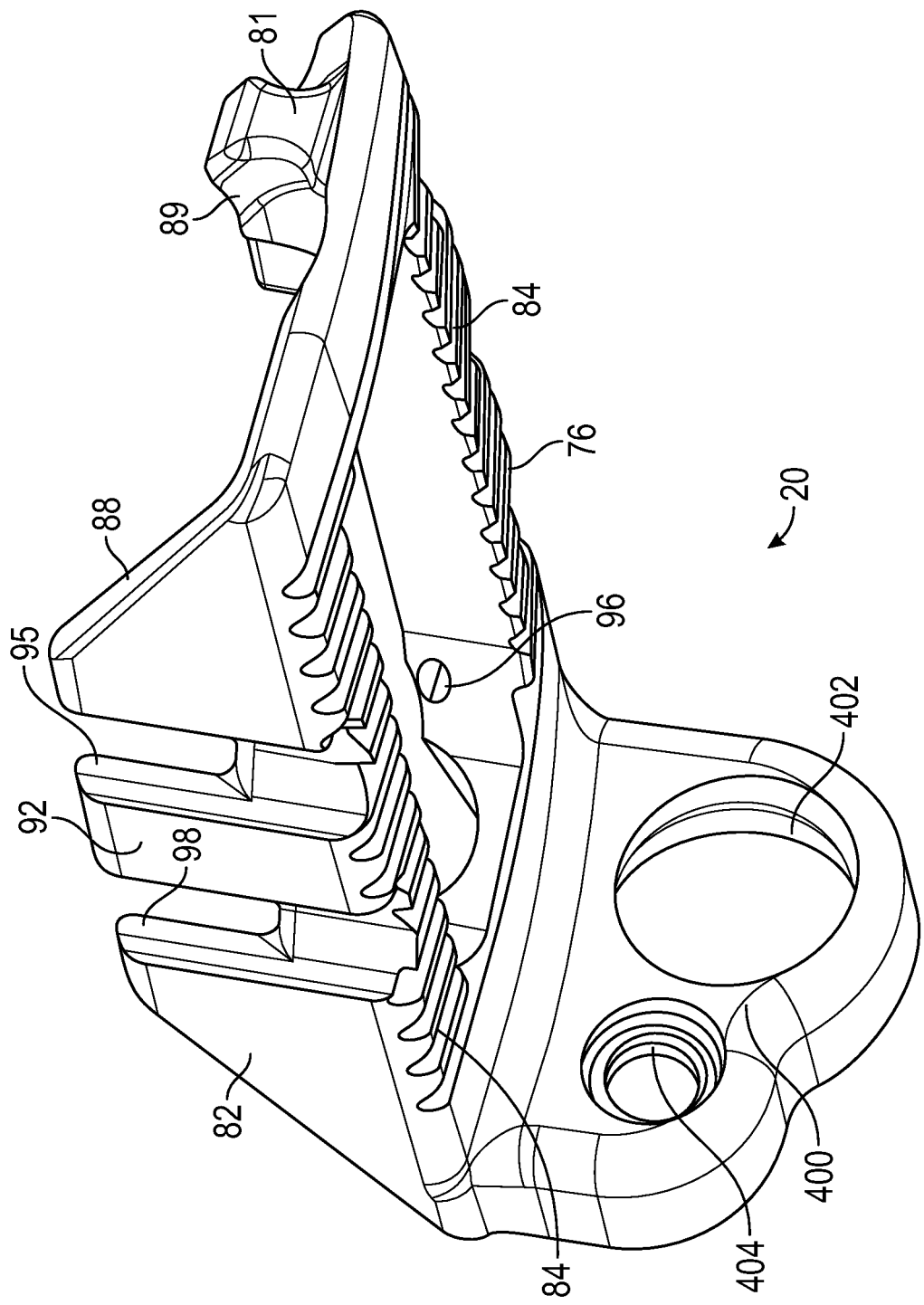
FIG. 22 is another perspective view of the lower support of the implant of FIG. 1 according an example embodiment.

Referring now to FIGS. 21 and 22, the lower support 20 is shown according to an example embodiment. In this example embodiment, the lower support 20 includes a lower surface 76, a front portion 79, a rear portion 81 opposite the front portion 79, a first side 80, and a second side 82 opposite the first side 80. In this example embodiment, the lower support 20 further includes a plurality of ridges 84 on the lower surface 76. The series of ridges 84 may create a surface roughness that provides additional stability of the implant 10 once installed.

The lower support 20 further includes a first ramp 85, a second ramp 86, a third ramp 87, and a fourth ramp 88. The first ramp 85 and the second ramp 86 are proximate the front portion 79, and are configured to engage the second ramped surface 27 and the fourth ramped surface 29 of the front component 12. In some example embodiments, the first ramp 85 will slide along the second ramped surface 27 and the second ramp 86 will slide along the fourth ramped surface 29 as the implant 10 expands from a first position to a second position, as will be discussed further herein.

The lower support 20 further includes a third ramp 87 and a fourth ramp 88 proximate the rear portion 81 of the lower support 20. The third ramp 87 and the forth ramp 88 are configured to engage the lower ramp 150 of the rear component 14. In some example embodiments, the third ramp 87 and the fourth ramp 88 will slide along the lower ramp 150 of the rear component 14 as the implant 10 expands from a first position to a second position, as will be discussed further herein.

The lower support 20 may further includes a guide rail 89 proximate the rear portion 51. The guide rail 89 is configured to be received by the first guide groove 146 of the rear component 14. In some embodiments, the guide rail 89 will translate within the first guide groove 146 of the rear component 14 as the implant 10 expands from a first position to a second position, as will be discussed further herein. Further, the lower support 20 may include a first side projection 90, a second side projection 91, and a first side slot 93 proximate the first side 80. Further, the lower support 20 may include a third side projection 92, a second side slot 94, and a third side slot 95 proximate the second side 82. Additionally, the lower support 20 may include a pin aperture 97 configured to receive a pin 67, as will be discussed further herein.

In some embodiments, the lower support 20 further includes a lower mounting plate 400 proximate the front portion 79. In this example embodiment, the lower mounting plate 400 is integrated into the lower support 20, such that the lower support 20 and lower mounting plate 400 are manufactured as one piece. For example, the lower support 20 and lower mounting plate 400 may be 3D printed as a single piece. The lower mounting plate 400 may include an unthreaded bore 402 configured to receive an anchoring member, such as a bone screw 22 (see FIG. 23), as will be discussed further herein. Additionally, the upper mounting plate 300 may include a threaded bore 304 configured to receive a retention member 24 (see FIG. 23), as will be discussed further herein.

Figure 23:
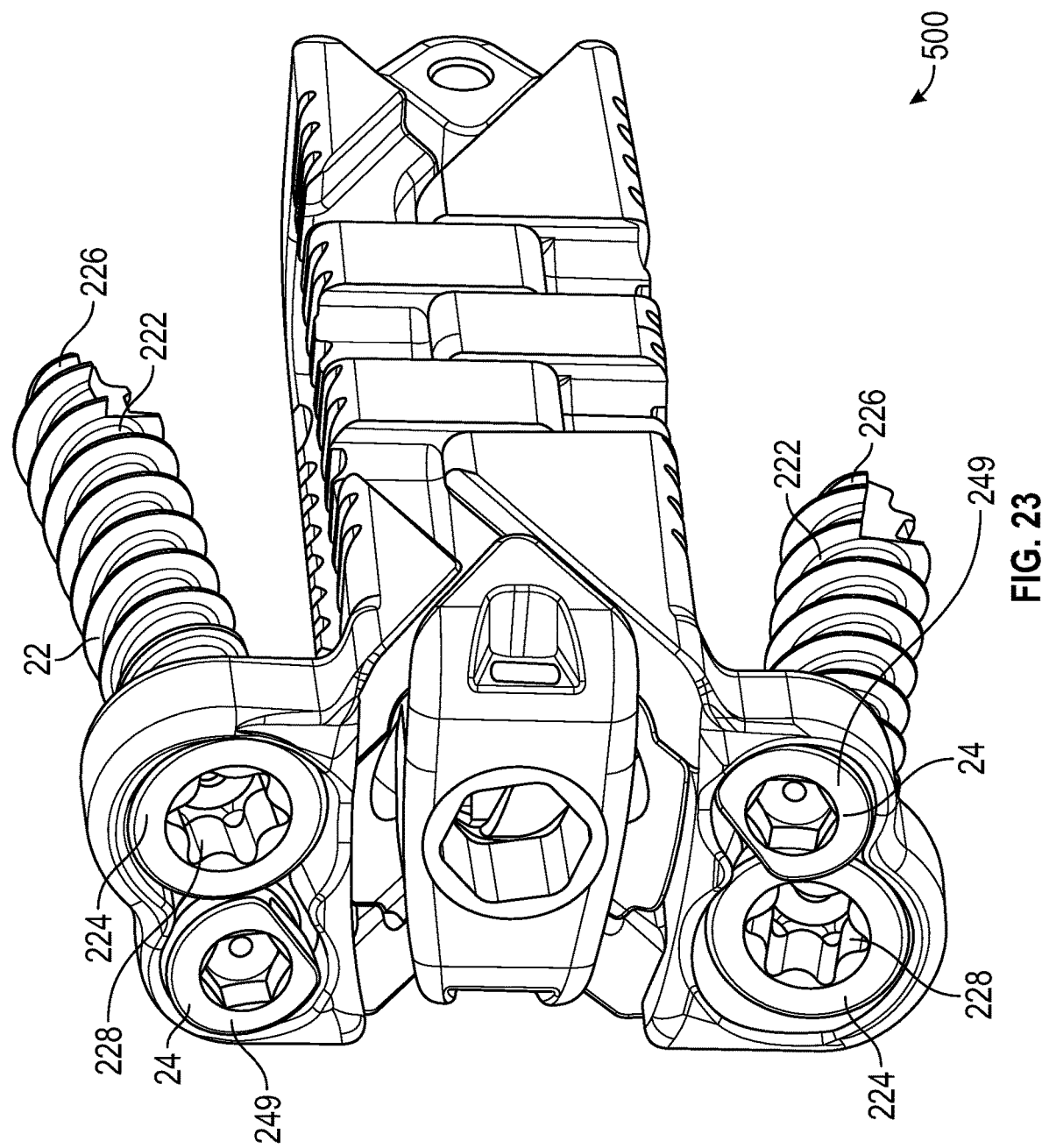
FIG. 23 is a perspective view of the implant of FIG. 1 with a plurality of retention members according to another example embodiment.
Figure 24:
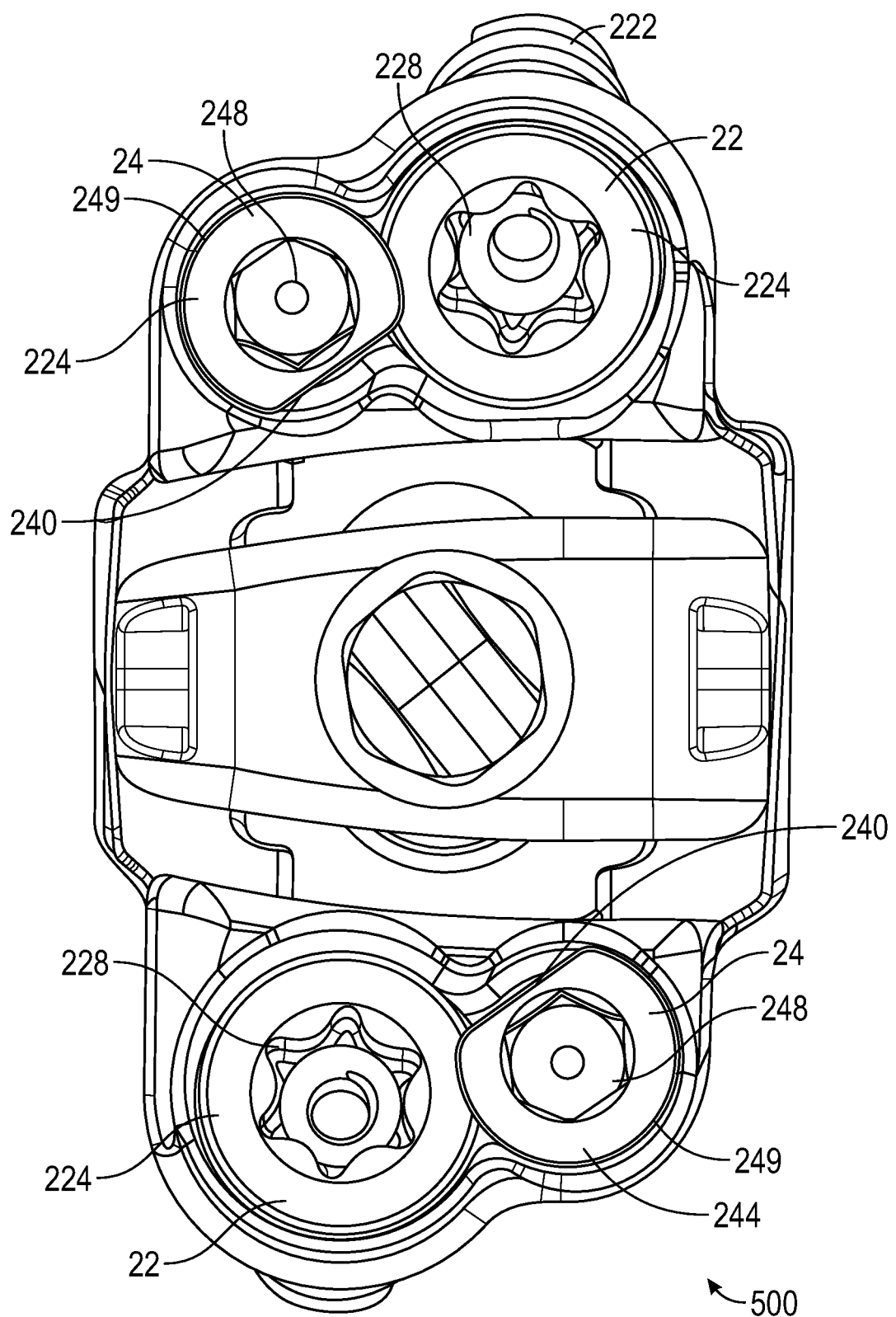
FIG. 24 is a front view of the implant of FIG. 23 according to an example embodiment.

Referring now to FIGS. 23 and 24, the implant 10 is shown with a plurality of anchoring members. According to some example embodiments, the implant 10 may contain at least one anchoring member used to secure the implant 10 inside a patient. For example, the anchoring member may be a bone screw 22. The example embodiment shown in FIG. 23 shows an implant 10 with two bone screws 22 used as anchoring members. According to this example embodiment, each bone screw 22 includes a linear, externally threaded shaft 222, a head 224 at a first end, and a tip 226 at a second end opposite the first end. In some embodiments, the tip 226 is pointed. In some embodiments, the diameter of the bone screw 22 remains constant from the head 224 to the tip 226. The head 224 further includes a socket 228 that is configured to receive an installation tool. While this example embodiment has a torx drive socket 228, it should be appreciated that the socket 158 can be designed to receive several different types of hand tools, including a slotted screwdriver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

Once the bone screw 22 is inserted into a bone, as will be discussed further herein, a retention screw 24 may be used to prevent a back out of the bone screw 22. In an example embodiment, such as the embodiment shown in FIG. 24, the retention screw 24 may include a head 244, a tool port 248, and a threaded shaft 242 (see. FIG. 11). The threaded shaft 242 may be screwed into either the threaded bore 304 of the upper mounting plate 300 and/or the threaded bore 404 of the lower mounting plate 400, as shown in FIG. 24.

The head 244 further includes a flat portion 240 and a rounded shoulder portion 249. In some embodiments, when the flat portion 240 is proximate the head 244 of the bone screw 22, the retention screw 24 is not in contact with the bone screw 22. However, the retention screw 24 may be tightened into the threaded bore 304 of the upper mounting plate 300 and/or the threaded bore 404 of the lower mounting plate 400, such that the rounded shoulder portion 249 is proximate to the bone screw 22. In some embodiments, when the retention screw 24 is tightened into the threaded bore 304 of the upper mounting plate 300 or the threaded bore 404 of the lower mounting plate 400, the underside of the rounded shoulder portion 249 is in contact with the head 224 of the bone screw 22. In doing so, the retention screw 24 may be used to prevent back out of the bone screw 22.

In the example embodiment shown in FIG. 24, the retention screw 24 includes a tool port 248 configured to receive a hex head driver. It should be appreciated that the tool port 248 can be designed to receive several different types of hand tools, including a slotted screwdriver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

Figure 25:
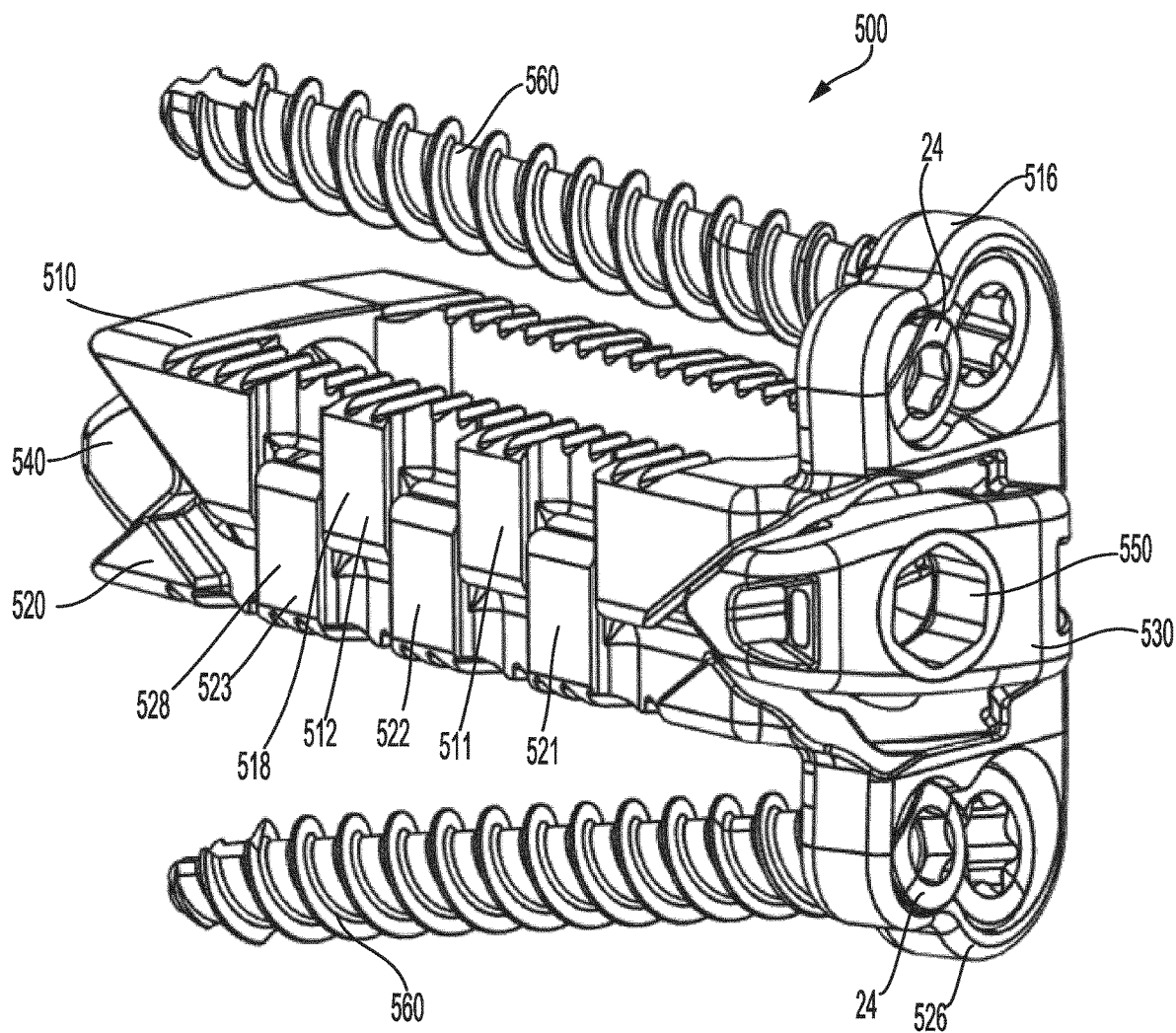
FIG. 25 is a perspective view of an implant according to another example embodiment.
Figure 26:
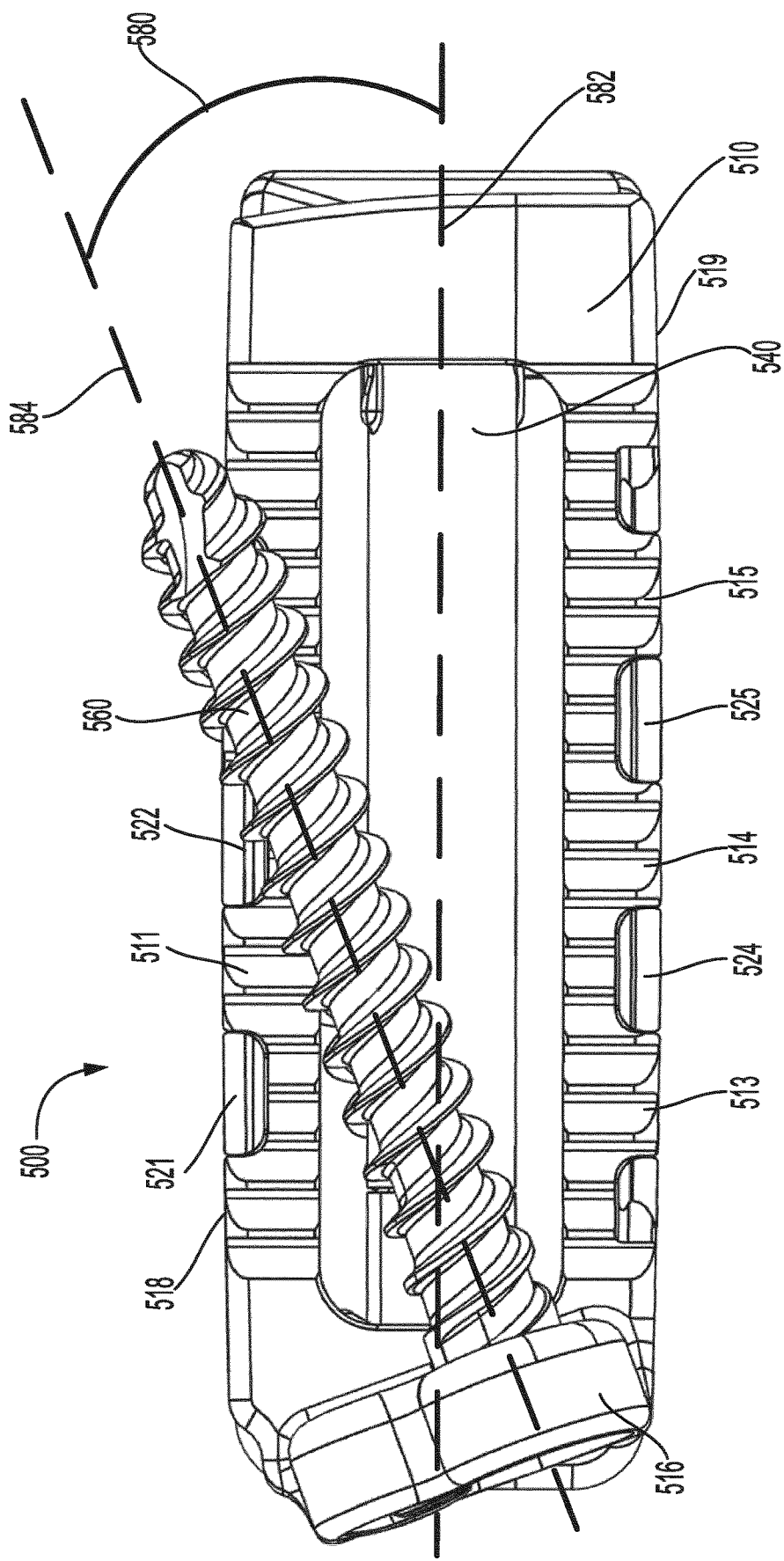
FIG. 26 is a top view of the implant of FIG. 25 according to an example embodiment.

Referring now to FIGS. 25 and 26, an implant 500 is shown according to an example embodiment. The implant 500 is usable, for example, between and/or within vertebral bodies of the spine. It should be understood that the implant 500 may, in some embodiments, be usable in other portions of the body in addition to the spine, and all such applications are to be understood to be within the scope of the present disclosure.

According to an exemplary embodiment, the implant 500 includes a first, or front component 530 (e.g., a first wedge member), a second, or rear component 540 (e.g., a second wedge member), and a third, intermediate, or control member 550, which collectively form a control assembly that extends along a longitudinal axis 582 of the implant 500. A first, or upper support 510 (e.g., an upper plate, support member, assembly, etc.) and a second, or lower support 520 (e.g., a lower plate, support member, assembly), are coupled to the control assembly and extend generally between the front component 530 and rear component 540. In certain embodiments, the upper support 510 may be identical to the lower support 520, which may reduce manufacturing costs of the implant 500.

The control assembly can be used to expand the implant 500 between at least a first, collapsed position and a second, expanded position, as shown in FIG. 25. The control assembly, including the front component 530, the rear component 540, and the control member 540, can be used to control the implant height (e.g., a support height defined by the upper and lower grooved/toothed surfaces of the implant), wherein the height of the implant 500 is the vertical distance between an outer or top surface of upper support 510 and outer or lower surface of lower support 520. The control assembly is configured to interface with the upper support 510 and the lower support 520 to control the height of the implant 500 in a similar manner as described above with respect to the implant 10 shown in FIGS. 1-10.

The upper support includes a first side projection 511 and a second side projection 512 on a first lateral side 518 of the upper support 510. The upper support 510 further includes a third side projection 513, a fourth side projection 514, and a fifth side projection 515 on a second lateral side 519 of the upper support 510. The lower support 520 includes a first side projection 521, a second side projection 522, and a third side projection 523 on a first lateral side 528 of the lower support 520. The lower support 520 further includes a fourth side projection 524 and a fifth side projection 525 on a second lateral side 529 of the lower support. As the implant 500 expands from the first, collapsed position to the second, expanded position, the plurality of side projections 511, 512 of the upper support 510 slidably interface with the plurality of side projection 521, 522, 523 of the lower support 520. Additionally, as the implant 500 expands from the first, collapsed position to the second, expanded position, the plurality of side projections 513, 514, 515 of the upper support 510 slidably interface with the plurality of side projection 524, 525 of the lower support 520. The plurality of side projections 511, 512, 513, 514, 515 of the upper support 510 and the plurality of side projections 521, 522, 523, 524, 525 of the lower support 520 may provide the implant 500 with additional mechanical stability by preventing the various components from shifting, including preventing lateral movement of the upper support 510 relative to the lower support 520.

The upper support 510 may further include a mounting plate 516 configured to receive a retention member 24 and an anchoring member 560, such as a bone screw. The lower support 520 may also included a mounting plate 526 configured to receive a retention member 24 and an anchoring member 560, such as a bone screw. In some embodiments, such as the embodiment shown in FIGS. 25 and 26, the mounting plate 516 of the upper support 510 and the mounting plate 526 of the lower support 520 may be angled, such that when the anchoring member 560 is inserted into the mounting plate 516, 526, a center-line trajectory 584 of the anchoring member 560 is not parallel with the longitudinal axis 582 of the implant 500. For example, as shown in FIG. 26, the center-line trajectory 584 and the longitudinal axis 582 form a plate angle 580. In certain embodiments, such as the implant 10 shown in FIGS. 1-10, the plate angle 580 may be 0 degrees. However, in other embodiments, such as the implant 500 shown in FIGS. 25 and 26, the plate angle 580 may be around 20 to 30 degrees. The plate angle 580 may be vary from 0 degrees to 90 degrees, depending on the application of implant 500. The plate angle 580 may vary based on the location an implant is being inserted into, and also based upon the insertion angle into the patient. For example, the implant 500 may be used in an Anterior to Psoas (ATP) Fusion surgery.

Figure 27:
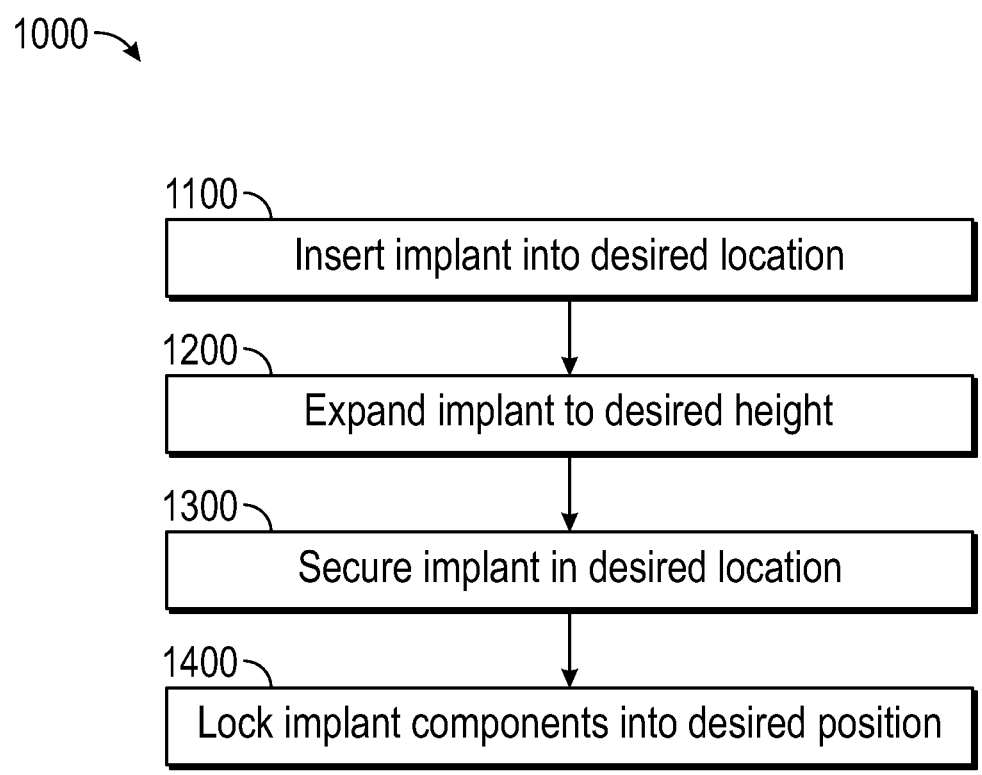
FIG. 27 is a flow chart for a method of installing an implant according to an example embodiment.

Referring now to FIG. 27, a method of installing an implant 1000 is shown according to an example embodiment. If should be appreciated that the method shown is exemplary in nature, and should not be construed as limiting. Additional steps may be included in the method, and steps shown may be omitted and/or performed in any suitable order. While reference is made to specific implants, it should be appreciated that this method may apply to any suitable implant.

Step 1100 involves inserting an implant into a desired location. For example, step 1100 may involve inserting the implant 10 shown in FIG. 1 into a patient. In some embodiments, step 1100 involves inserting the implant 10 between two adjacent vertebrae in a patient's spinal column. In certain embodiments, the implant 10 is inserted into a patient's spinal column through the lateral side of a patient. In some embodiments, the implant 10 may be used in a lateral lumbar interbody fusion (LLIF) surgery. For example, an incision in the lateral side of a patient may be made, and the implant 10 may be inserted into the patient's spine. In this example embodiment, the rear nose 142 of the rear component 14 may be inserted between two adjacent vertebrae in the patient's spinal column. In some embodiments, a surgeon or other user may use an installation tool to grip the installation tool interfaces 35, 37 of the implant 10, and the installation tool may then be used to insert the implant 10 into a desired location.

Figure 4:
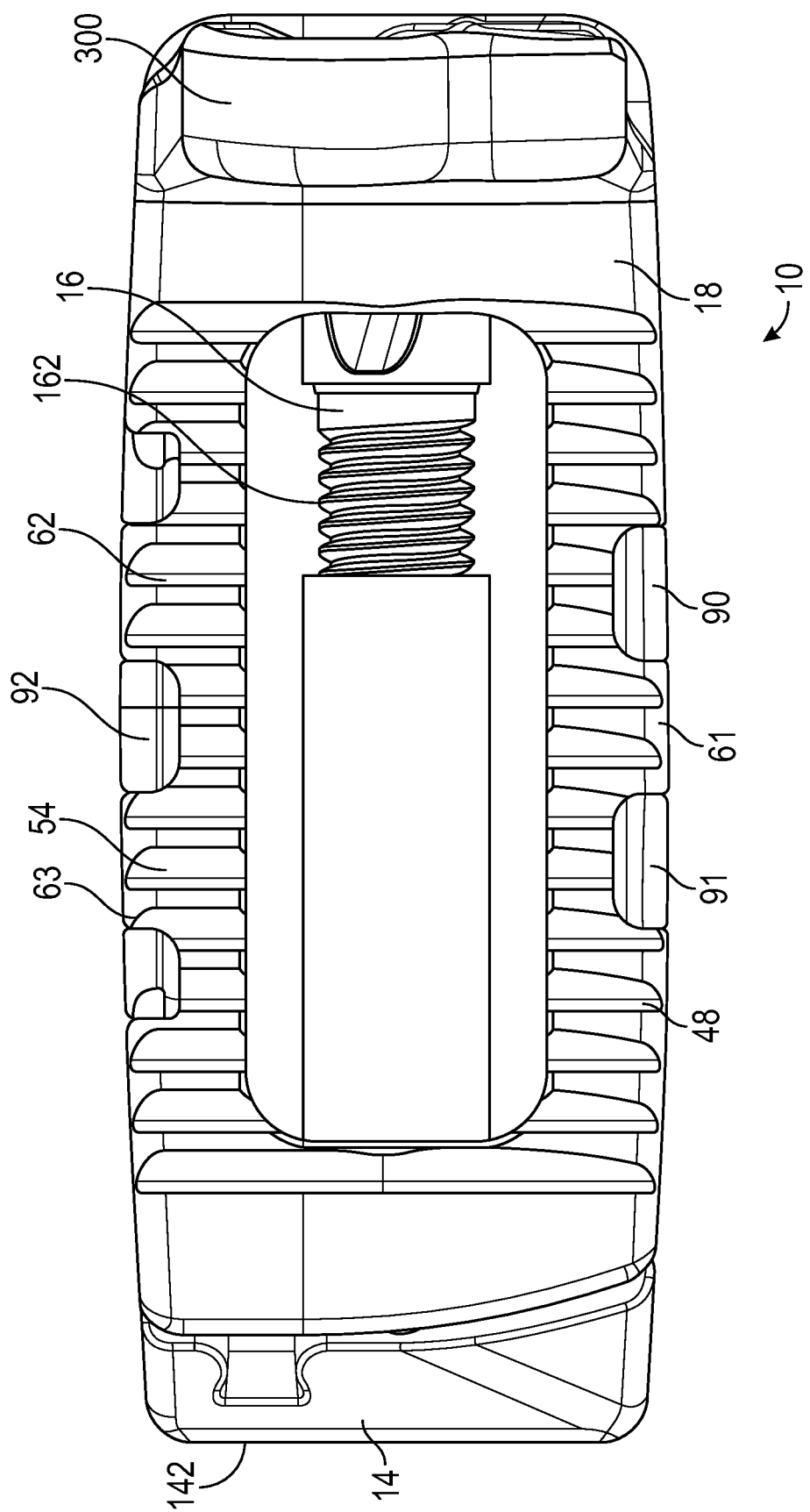
FIG. 4 is a top view of the implant of FIG. 1 in a collapsed position according to an example embodiment.
Figure 5:
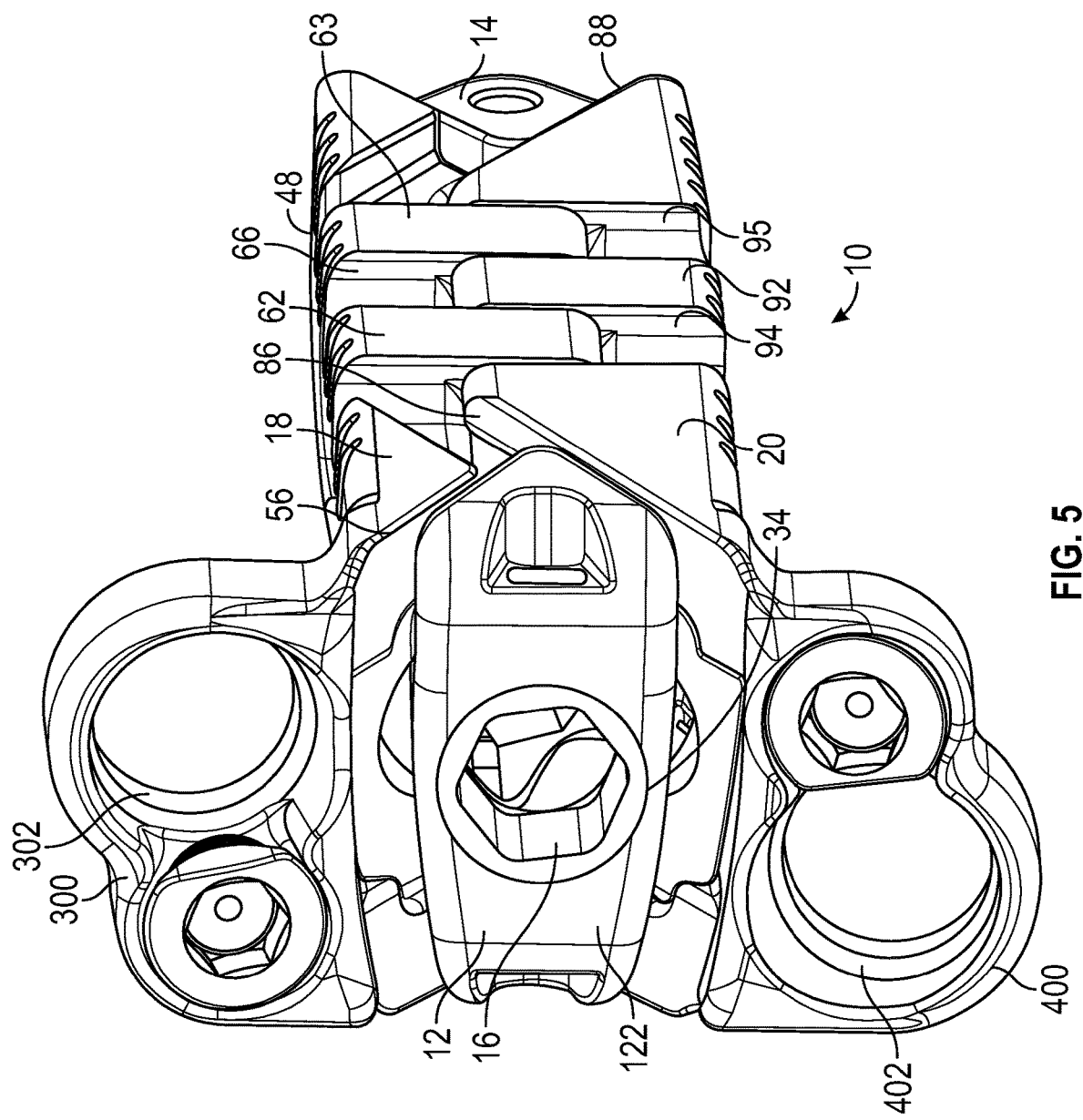
FIG. 5 is a perspective view of the implant of FIG. 1 in an expanded position according to an example embodiment.
Figure 6:
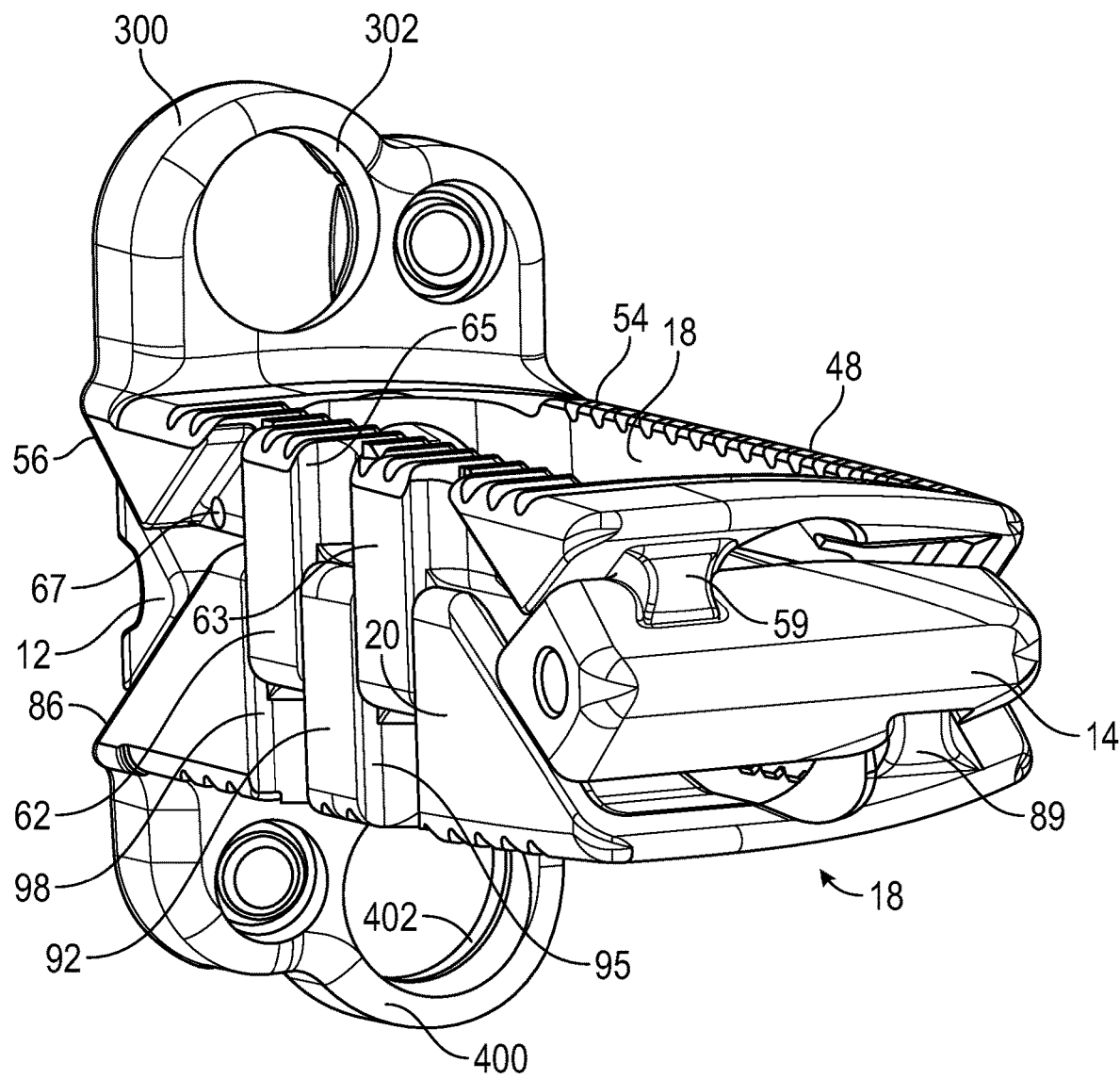
FIG. 6 is another perspective view of the implant of FIG. 1 in an expanded position according to an example embodiment.
Figure 7:
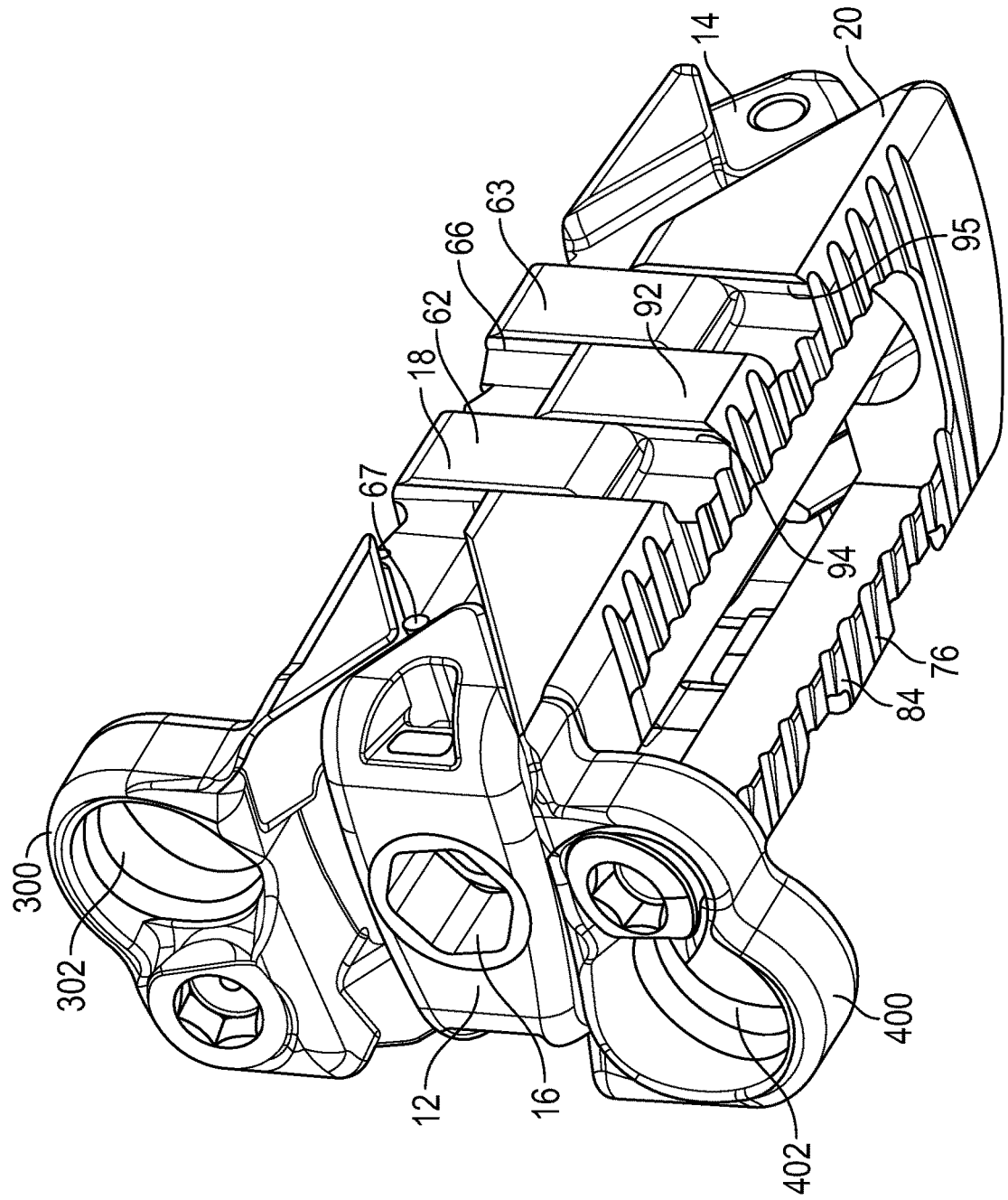
FIG. 7 is another perspective view of the implant of FIG. 1 in an expanded position according to an example embodiment.
Figure 8:
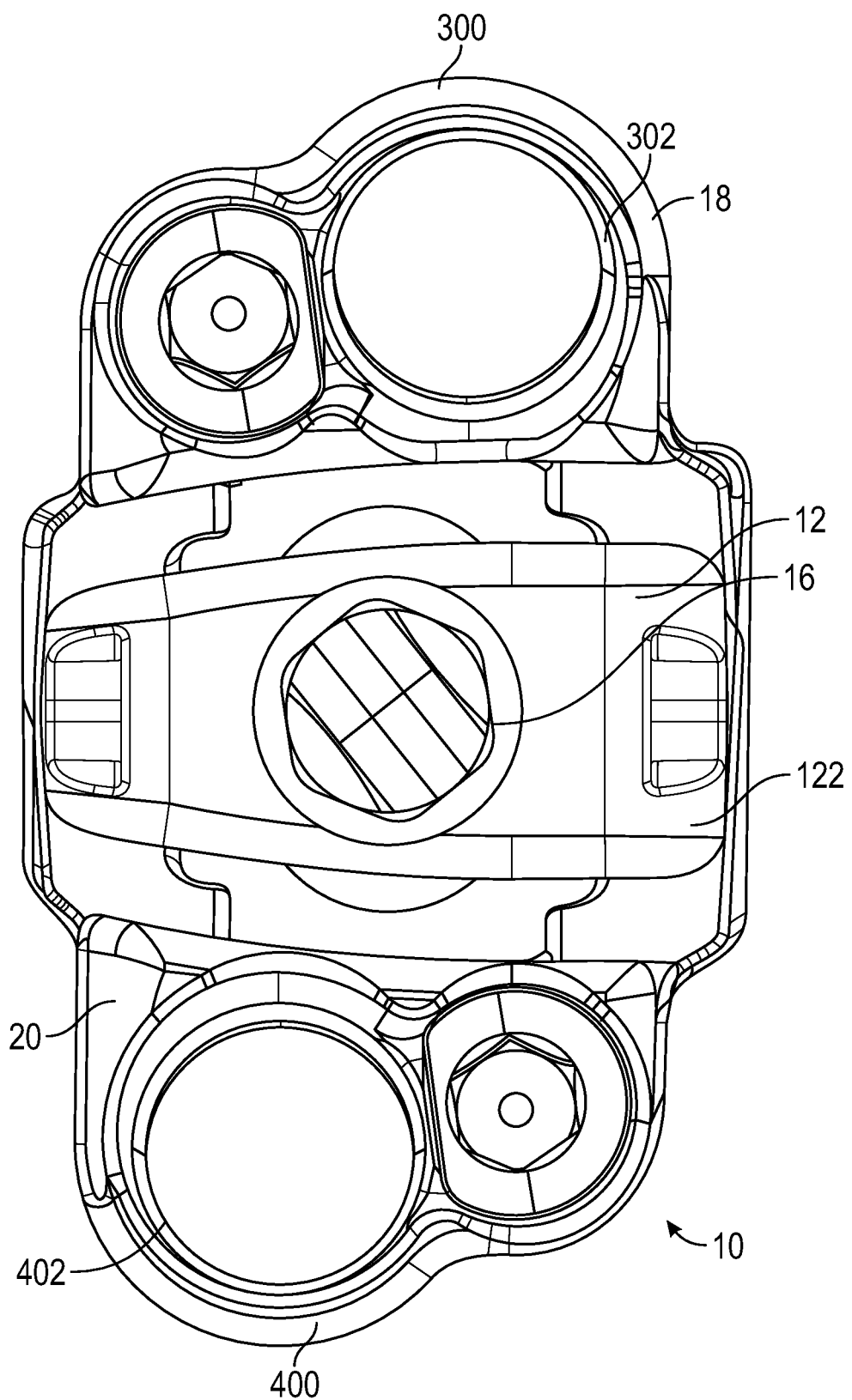
FIG. 8 is a front view of the implant of FIG. 1 in an expanded position according to an example embodiment.
Figure 9:
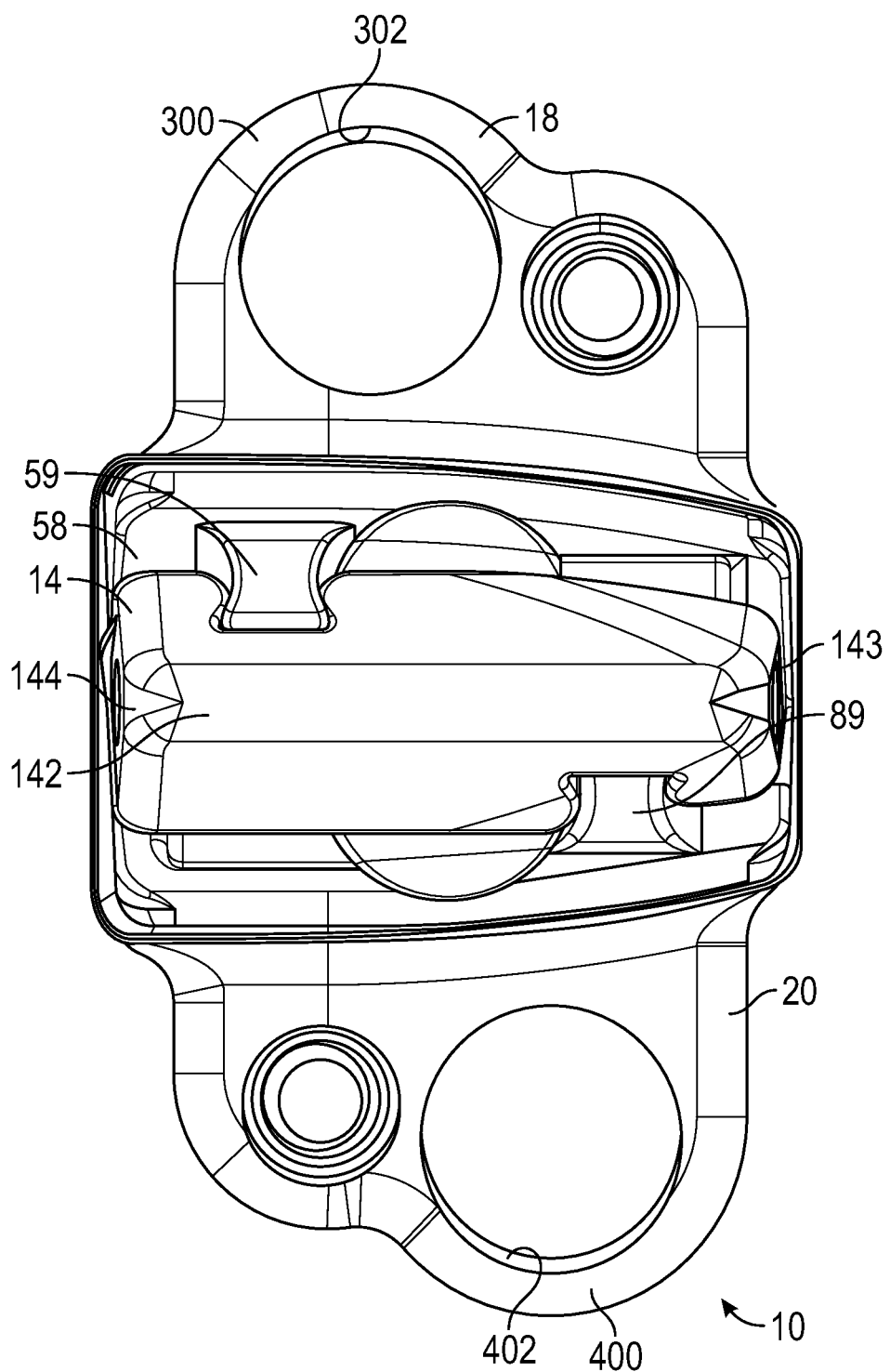
FIG. 9 is a rear view of the implant of FIG. 1 in an expanded position according to an example embodiment.

In some embodiments, when the implant 10 is inserted, the implant 10 is in a first, collapsed position, as shown in FIGS. 1-4. According to some embodiments, when the implant 10 is in the first, collapsed position, the control member 16 is received by the control bore 34 of the front component 12. The control member 16 may be received by the control bore 34 prior to the implant 10 being inserted. The control member 16 extends into a central cavity of the implant 10, and the threaded shaft 162 of the control member 16 is received by the threaded bore 145 of the rear component 14, as shown in FIG. 4. In this example embodiment, the threaded shaft 162 of the control member 16, and the threaded bore 145 of the rear component 14 are threaded such that turning the control member 16 in a clockwise direction will cause the head 164 of the control member 16 to move in a direction towards the rear nose 142 of the rear component 14. However, in other embodiments, the threaded shaft 162 and threaded bore 145 may be threaded such that turning the control member 16 in a counter-clockwise direction will cause the head 164 of the control member 16 to move in a direction towards the rear nose 142 of the rear component 14. In further embodiments, the rear component 14 and the control member 16 may mechanically engage using other mechanisms, such as a zipper mechanism, a plurality of teeth on the shaft 162 and the bore 145, etc. to allow an operator to manipulate the position of shaft 162 within the bore 145.

In an example embodiment, the control member 16 and the rear component 14 engage the upper support 18 and the lower support 20 in the first, collapsed position. For example, the guide rail 59 of the upper support 18 may be received by the second guide groove 147 of the rear component 14. Further, the guide rail 89 of the lower support 20 may be received by the first guide groove 146 of the rear component 14. In some embodiments, the guide grooves 146, 147 may prevent the upper support 18 from expanding away from the lower support 20 when the implant 10 is in the first, collapsed position. Further, the first ramped surface 26 and the first projection 30 of the front component 12 may engage the first ramp 55 of the upper support 18 in the first, collapsed position. Similarly, the third ramped surface 28 and the third projection 32 of the front component 12 may engage the second ramp 56 of the upper support 18 in the first, collapsed position. Additionally, the second ramped surface 27 and the second projection 31 of the front component 12 may engage the first ramp 85 of the lower support 20 when the implant 10 is in the first, collapsed position. Similarly, the fourth ramped surface 29 and the fourth projection 33 may engage the second ramp 86 of the lower support 20 when the implant 10 is in the first, collapsed position. These ramps and projections may prevent the upper support 18 and the lower support 20 from undesirably shifting laterally or expanding away from one another when the implant 10 is in the first, collapsed position.

In certain embodiments, such as the embodiments shown in FIGS. 13 and 14, the projections 30, 31, 32, 33 may be dovetail shaped. The dovetail shape may help keep the various components of the implant from undesirably shifting relative to one another.

Further, in some embodiments, when the implant 10 is in the first, collapsed position, the upper support 18 interfaces with the lower support 20 as shown in FIGS. 1 and 4. In this example embodiment, the second side projection 62 of the upper support 18 is positioned between the first side projection 90 and the second side projection 91 of the lower support 20. Further, the third side projection 92 of the lower support 20 is positioned between the second side projection 62 and third side projection 63 of the upper support 18 in the first, collapsed position.

Figure 10:
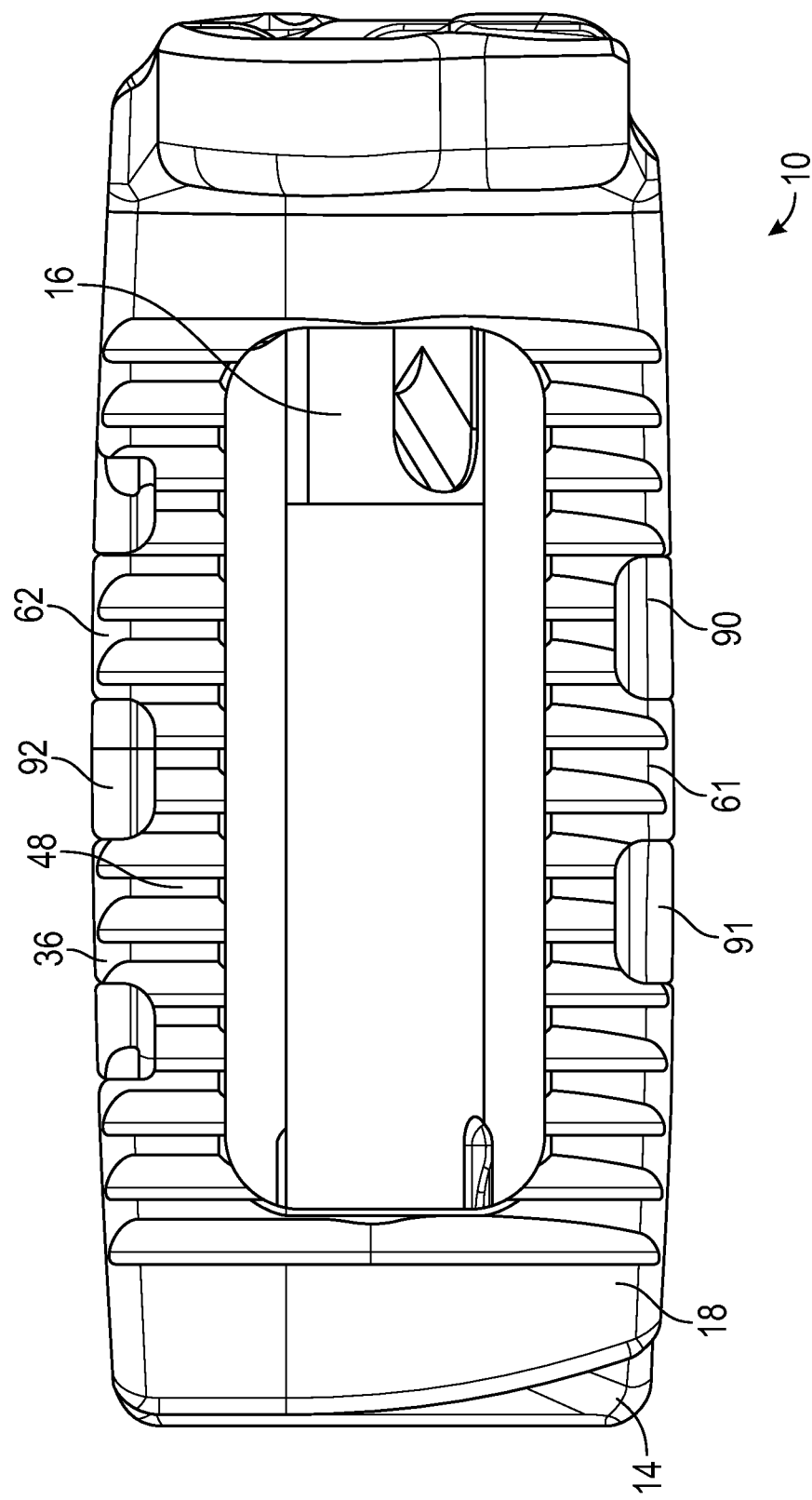
FIG. 10 is a top view of the implant of FIG. 1 in an expanded position according to an example embodiment.

Step 1200 involves expanding an implant to a desired height. For example, after the implant is inserted between two adjacent vertebrae, the implant may be expanded. In some embodiments, the implant 10 may be expanded to a second, expanded position as shown in FIGS. 5-9. In this example embodiment, a person may expand the implant 10 from a first, collapsed position to a second, expanded position using the control member 16. For example, the person may use an expansion tool that engages with the tool port 166 of the control member 16. For example, the expansion tool may be a hex head screw driver. The person may then use the installation tool to turn the control member 16, for example, in a clock-wise direction. In this example embodiment, the threaded shaft 162 of the control member 16, and the threaded bore 145 of the rear component 14 are threaded such that turning the control member 16 in a clockwise direction will cause the head 164 of the control member 16 to move in a direction towards the rear nose 142 of the rear component 14. As the control member 16 is turned, the threaded shaft 162 will screw into the threaded bore 145, until the threaded shaft 162 is completely within rear component 14, as shown in FIG. 10. It should be appreciated that, while the Figures generally show control member 116 threadingly engaging the rear component 14, in other embodiments, other adjustment mechanisms may be used (e.g., ratchet mechanisms, indents/detents, etc.). In these embodiments, the control member 16 may be manipulated (e.g., urged, turned, pushed, rotated, etc.) to control relative movement between the upper support 18 and the lower support 20.

As the head 164 of the control member 16 moves towards the rear nose 142 of the rear component 14, the guide rail 59 of the upper support 18 will slide within the second guide groove 147 of the rear component 14. Further, the guide rail 89 of the lower support 20 will slide within the first guide groove 146 of the rear component 14. Further, the first ramp 55 of the upper support 18 will slide along the first ramped surface 26 of the front component 12, and the second ramp 56 will slide along the third ramped surface 28 of the front component 12. Additionally, the first ramp 85 of the lower support 20 will slide along the second ramped surface 27 of the front component 12, and the second ramp 86 of the lower support 20 will slide along the fourth ramped surface 29 of the front component 12. Thus, as the control member 16 is screwed into the threaded bore 145 of the rear component 14, the upper support 18 and the lower support 20 will expand away from each other at least in part due to the ramped surfaces 26, 27, 28, 29 on the front component 12, the rear component 14, the upper support 18, and the lower support 20.

Further, it should be appreciated that the expansion profile of an implant may be customized in part by changing the angles of the various ramped surfaces. Using the implant in various locations may require a custom expansion profile. For example, if the implant is inserted into a patient's spine, the implant expansion profile may be customized to match the curvature of the patient's spine at the desired location that the implant is to be implanted into. In some example embodiments, the ramped surfaces 26, 27, 28, 29 of the front component 12 may have a much higher angle (i.e., the angle that upward angled surface and the downward angle surface form) than the ramped surfaces 26, 27, 28, 29 of the rear component 14. In this example embodiment, turning the control member 16 will cause the implant 10 to expand more near the front component 12 than near the rear component 14. In this example embodiment, the implant 10 height will be larger near the front component 12 than near the rear component 14. It should be appreciated that further customization of the expansion profile of an implant 10 may be accomplished by adjusting the angle of ramped surfaces 26, 27, 28, 29 on the front component 12, the rear component 14, the upper support 18, and the lower support 20.

Step 1300 involves securing the implant in a desired location within a patient. For example, step 1300 may involve securing the implant to the two adjacent vertebrae that the implant was inserted between. In an example embodiment, the implant 10, as shown in FIG. 23, may be secured to adjacent vertebrae using bone screws 22. For example, the implant 10 may be inserted between two vertebrae, and expanded to a desired height. In this example embodiment, the top surface 48 of the upper support 18 may engage the upper vertebrae and the lower surface 76 of the lower support 20 may engage the lower vertebrae. A first bone screw 22 may be driven through the unthreaded bore 302 of the upper mounting plate 300 and into an adjacent vertebrae. A second bone screw 22 may then be driven through the unthreaded bore 402 of the lower mounting plate 400 and into another adjacent vertebrae. It should be appreciated that the bone screws 22 may inserted into the unthreaded bore 402 of the lower mounting plate 400, securing the implant 10 to the lower vertebrae before the first bone screw 22 is through the unthreaded bore 302 and into the upper vertebrae.

It should be appreciated that step 1300 may occur before, after, or in conjunction with step 1200. For example, in one embodiment, the implant 10 may be secured to two adjacent vertebrae while in a first, collapsed position, and then expanded to a desired height. Alternatively, the implant 10 may be secured to one vertebrae while in a first, collapsed position, then expanded to a desired height, and then secured to a second vertebrae. Additionally, the implant 10 may be used without any anchoring members.

Step 1400 involves locking the implant components into a desired position. In some embodiments, for example, a plurality of retention wedges 127 and pins 67 (see FIG. 11) may be used to secure components in place. For example, once the implant 10 is set to a desired height, a first retention wedge 127 and a second retention wedge 127 may be driven (e.g., pressure fit) into a first wedge slot 126 and a second wedge slot 126 on the front component 12. In this example embodiment, the retention wedges 127 are driven through the wedge slots 126 and into the groove 169 of the control member 16. In doing so, the control member 16 will be prevented from backing out. Therefore, the retention wedges 127 will prevent the implant 10 from further expanding or collapsing.

Further, the implant 10 may be locked into a desired position using retention pins 67. For example, once the implant 10 is in a desired position, a first retention pin 67 may be driven (e.g., press fit) into the pin aperture 68 on the upper support 18 and a second retention pin 67 may be driven (e.g., press fit) into the pin aperture 96 of the lower support 20. In doing so, the retention pins 67 may extend into the center cavity of the implant 10, thereby preventing the front component 12 from moving closer to the rear component 14, thereby preventing over expansion of the implant 10. Additionally, the retention pins 67 may prevent the implant 10 from collapsing by preventing the lower support 20 and the upper support 18 from returning to the first, collapsed position.

Step 1400 may further include locking anchoring members into place. For example, the bone screws 22 of the implant 10 shown in FIG. 24, may be locked into place using the retention members 24. For example, before the implant 10 is installed, a first retention member 24 may be partially screwed into the threaded bore 304 of the upper mounting plate 300 and a second retention member 24 may be threaded into the threaded bore 404 of the lower mounting plate 400. In this example embodiment, the first retention member 24 may be screwed into the threaded bore 304 such that the flat portion 240 of the retention member 24 is proximate the unthreaded bore 302. Additionally, the second retention member 24 may be screwed into the threaded bore 404 such that the flat portion 240 of the retention member 24 is proximate the unthreaded bore 402. Once the implant 10 is in place, the bone screws 22 may be inserted into the unthreaded bores 302, 402 and driven into the adjacent vertebrae. Since the flat portion 240 of the retention members 24 is proximate the unthreaded bores 302, 402, the retention members 24 will not interfere with the bone screws 22 as the bone screws 22 are driven into the adjacent vertebrae. Once the bones screws 22 are secured, the retention members 24 may be turned using a tool. For example, in the embodiment shown in FIG. 24, the retention members 24 may be turned using a hex head screw driver. The retention members 24 may be turned such that the rounded should portion 249 is proximate the head 224 of the bone screw 22. In doing so, the underside of the head 244 of the retention member 24 may be pressed up against the head 224 of the bone screw 22, thereby preventing the bone screw 22 from backing out.

Referring now to the Figures generally, the various embodiments disclosed herein provide expandable implants including a lower support and an upper support adjustably coupled to the lower support and movable between a first, collapsed position, and a second, expanded position. Further, a rear component and a control shaft rotatably received by the rear component is disclosed, where rotation of the control shaft causes relative movement of a front component relative to the rear component.

In some embodiments, the upper support moves in a linear fashion relative to the lower support. In other embodiments, the upper support may move in a non-linear fashion relative to the lower support. In some embodiments, a single control member and control shaft are utilized. In other embodiments, multiple (e.g., 2) control members and control shafts are utilized. In some embodiments, the multiple control channels are parallel and straight. In other embodiments, the control channels are non-parallel and straight (e.g., angled toward each other). In further embodiments, the control channels are non-parallel and non-straight such that the adjustable member moves in a non-linear fashion relative to the base member.

In some embodiments, the control shaft includes a control thread corresponding to each control member. As such, while in some embodiments the control shaft includes a single control thread, in other embodiments the control shaft includes multiple (e.g., first and second) control threads. In some embodiments, the control threads are like-threaded. In other embodiments, the control threads have different threads. For example, in some embodiments, a first control thread is opposite-handed from a second control thread. In further embodiments, a first control thread has a different pitch from a second control thread. In yet further embodiments, a first control thread is different handed and has a different pitch from a second control thread.

In some embodiments, one or both of the lower support and the upper support include projections/grooves to provide a gripping surface intended to facilitate gripping adjacent portions of bone. In further embodiments, one or both of the lower support and the upper support include one or more apertures and/or cavities configured to promote bone growth in and around the lower support and the upper support. In some embodiments, the apertures extend from a top, bottom, and/or side surface of the lower support and the upper support and to a central cavity of the implant.

According to any of the embodiments disclosed herein, one or more bone screws may be included and positioned to extend through one or both of the lower support and the upper support and into adjacent portions of bone. In some embodiments, multiple bone screws are used. A first bone screw may extend through the adjustable member and into a first portion of bone, and a second bone screw may extend through the base member and into a second portion of bone. In further embodiments, multiple bone screws are accessible and manipulatable by way of the front face of the implant defined by one or both of the adjustable member and the base member. A head and tool port of the control shaft may further be accessible by way of the front face of the implant.

In various embodiments, any suitable configuration of the control shaft/control member(s)/control channel(s) may be utilized. In some embodiments, an at least partially spherical control member threadingly engages a threaded control shaft and translates both along the control shaft and within the control channel. In other embodiments, the control member is non-spherical and is received at least partially on or in a control rail or control channel provided by the adjustable member, such that the control member translates along both the control shaft and the control channel or control rail.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of some features described and claimed without restricting the scope of these features to the precise numerical ranges provided. Accordingly, these terms should be interpreted as indicating that insubstantial or inconsequential modifications or alterations of the subject matter described and claimed are considered to be within the scope of the application as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on hardware systems chosen and on designer choice. All such variations are within the scope of the disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present application.

It should be appreciated that dimensions of the components, structures, and/or features of the present implants and installation instruments may be altered as desired within the scope of the present disclosure.

What is claimed is:

1. An implant, comprising:
   an upper support comprising an upper plate configured to receive a first anchoring member, the upper support comprising a first end, a second end opposite the first end, a first side extending between the first end and the second end, and a second side opposite the first side and extending between the first end and the second end, the upper plate configured to receive the first anchoring member such that a first center-line trajectory of the first anchoring member is angled towards the first side;
   a lower support coupled to the upper support in a non-hinged fashion, the lower support comprising a lower plate configured to receive a second anchoring member such that a second center-line trajectory of the second anchoring member is angled towards the first side;
   a control member comprising a head and a shaft and configured to control relative movement between the upper support and the lower support, the shaft defining an axis positioned at approximately a midpoint between the first and second sides of the upper support;
   a front portion comprising a first upper wedge surface configured to engage the first end of the upper support and a first lower wedge surface configured to engage the first end of the lower support, the front portion further configured to receive the head of the control member; and
   a rear portion comprising a second upper wedge surface configured to engage the second end of the upper support and a second lower wedge surface configured to engage the second end of the lower support, the rear portion further configured to engage a portion of the shaft, wherein manipulation of the control member causes the front portion to move relative to the rear portion, such that the upper support moves relative to the lower support;
   wherein the rear portion comprises a cylindrical member defining a cylindrical exterior surface extending from the second upper wedge surface and the second lower wedge surface and toward the front portion, wherein the cylindrical member comprises a threaded bore configured to threadingly receive the portion of the shaft.

2. The implant of claim 1, wherein the manipulation of the control member causes the front portion to move towards the rear portion and causes the upper support to move away from the lower support.

3. The implant of claim 1, wherein the upper support and lower support are identical.

4. The implant of claim 1, further comprising a plurality of anchoring members, including the first anchoring member and the second anchoring member.

5. The implant of claim 4, wherein
the implant has a longitudinal axis; and
the upper plate is configured to receive an anchoring member such that the center-line trajectory of the anchoring member and the longitudinal axis of the implant form a plate angle greater than 0 degrees.

6. The implant of claim 1, wherein the upper plate is further configured to receive a first retention member, and wherein the lower plate is further configured to receive a second retention member;
wherein the first retention member and the second retention member each comprises a flat portion and a rounded shoulder portion; and
wherein the rounded shoulder portion of the first retention member is configured to engage the head of the first anchoring member.

7. The implant of claim 1, wherein the upper support receives the first anchoring member at a position offset to the first side and the lower support receives the second anchoring member at a position offset to the second side.

8. An implant comprising:
an upper support configured to engage a first portion of bone, the upper support comprising an upper plate at a first end of the upper support and a side projection, the upper plate configured to receive a first anchoring member such that a first center-line trajectory of the first anchoring member is angled towards a first side of the implant to secure the upper support to the first portion of bone;
a lower support coupled to the upper support in a non-hinged fashion, the lower support being configured to engage a second portion of bone, the lower support comprising a lower plate at a first end of the lower support and a side slot configured to receive the side projection of the upper support, the lower plate configured to receive a second anchoring member such that a second center-line trajectory of the second anchoring member is angled towards the first side to secure the lower support to the second portion of bone;
a control assembly configured to control relative movement between the upper support and the lower support, the control assembly comprising;
a front portion configured to engage the upper support at only the first end of the upper support;
a rear portion configured to engage the upper support at only a second end of the upper support, the second end being opposite the first end; and
a control member adjustably engaging the front portion and the rear portion;
wherein during expansion of the implant a sidewall of the side projection remains proximate a sidewall of the side slot;
wherein the upper support wedgingly engages the control assembly only at a single longitudinal position of the front portion and a single longitudinal position of the rear portion and wherein the lower support wedgingly engages the control assembly only at the single longitudinal position of the front portion and the single longitudinal position of the rear portion.

9. The implant of claim 8, wherein manipulation of the control member causes the front portion to move towards the rear portion and causes the upper support to move away from the lower support.

10. The implant of claim 8, wherein the first anchoring member and the second anchoring member are bone screws.

11. The implant of claim 8, wherein the upper plate is further configured to receive a first retention member, and wherein the lower plate is further configured to receive a second retention member;
wherein each of the first retention member and the second retention member comprises a flat portion and a rounded shoulder portion; and
wherein the rounded shoulder portion of the first retention member is configured to engage a head of the first anchoring member.

12. An implant, comprising:
an upper support comprising an upper plate configured to receive a first bone screw, the upper support comprising a first end, a second end opposite the first end, a first side extending between the first end and the second end, and a second side opposite the first side and extending between the first end and the second end, the upper plate configured to receive the first bone screw such that a first center-line trajectory of the first bone screw is angled towards the first side;
a lower support comprising a lower plate configured to receive a second bone screw such that a second center-line trajectory of the second bone screw is angled towards the first side;
a control member comprising a head and a shaft and configured to control relative movement between the upper support and the lower support, the shaft defining an axis positioned at approximately a midpoint between the first and second sides of the upper support;
a front portion comprising a first upper surface configured to engage the upper support and a first lower surface configured to engage the lower support, the front portion further configured to receive the head of the control member; and
a rear portion comprising a second upper surface configured to engage the upper support, a second lower surface configured to engage the lower support, and a cylindrical member extending from the second upper surface and the second lower surface and defining a cylindrical exterior surface, the cylindrical member comprising threads configured to threadingly engage a portion of the shaft, wherein manipulation of the control member causes the front portion to move relative to the rear portion, such that the upper support moves relative to the lower support;
wherein the head of the control member comprises a tool port in communication with an opening on a side of the shaft to enable delivery of material to an interior of the implant via the tool port;
wherein the shaft comprises a non-threaded portion adjacent the head and a threaded portion adjacent the non-threaded portion, wherein opening is positioned on the non-threaded portion of the shaft.

13. The implant of claim 12, wherein the front portion engages the upper support at only a first end of the upper support and the rear portion engages the upper support at only a second end of the upper support opposite the first end.

14. The implant of claim 12, wherein the upper support comprises a side projection configured to be received in a side slot of the lower support such that during expansion of the implant opposite sidewalls of the side projection remain proximate corresponding sidewalls of the side slot.

\* \* \* \* \*